United States Patent
Nassar et al.

(10) Patent No.: US 10,845,213 B2
(45) Date of Patent: Nov. 24, 2020

(54) PAPER BASED ELECTRONICS PLATFORM

(71) Applicant: KING ABDULLAH UNIVERSITY OF SCIENCE AND TECHNOLOGY, Thuwal (SA)

(72) Inventors: Joanna Mohammad Nassar, Thuwal (SA); Galo Andrea Torres Sevilla, Thuwal (SA); Muhammad Mustafa Hussain, Austin, TX (US)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 182 days.

(21) Appl. No.: 16/067,659

(22) PCT Filed: Jan. 13, 2017

(86) PCT No.: PCT/IB2017/050202
§ 371 (c)(1),
(2) Date: Jul. 2, 2018

(87) PCT Pub. No.: WO2017/122178
PCT Pub. Date: Jul. 20, 2017

(65) Prior Publication Data
US 2019/0011288 A1 Jan. 10, 2019

Related U.S. Application Data

(60) Provisional application No. 62/278,545, filed on Jan. 14, 2016.

(51) Int. Cl.
*G01D 5/16* (2006.01)
*A61B 5/01* (2006.01)
(Continued)

(52) U.S. Cl.
CPC ............... *G01D 5/16* (2013.01); *A61B 5/01* (2013.01); *A61B 5/02141* (2013.01);
(Continued)

(58) Field of Classification Search
CPC .... G01D 5/16; G01D 21/00; B01L 3/502707; B01L 2400/0406; B01L 2300/0663;
(Continued)

(56) References Cited

U.S. PATENT DOCUMENTS 6,229,318 B1 * 5/2001 Suda .................... G01N 27/121
324/694
2010/0158544 A1 * 6/2010 Chabinyc ............... G03G 15/55
399/9

(Continued)

FOREIGN PATENT DOCUMENTS

WO 2013063445 A2 5/2013

OTHER PUBLICATIONS

International Search Report in related International Application No. PCT/IB2017/050202, dated May 4, 2017.

(Continued)

*Primary Examiner* — Giovanni Astacio-Oquendo
(74) *Attorney, Agent, or Firm* — Patent Portfolio Builders PLLC

(57) ABSTRACT

A flexible and non-functionalized low cost paper-based electronic system platform fabricated from common paper, such as paper based sensors, and methods of producing paper based sensors, and methods of sensing using the paper based sensors are provided. A method of producing a paper based sensor can include the steps of: a) providing a conventional paper product to serve as a substrate for the sensor or as an active material for the sensor or both, the paper product not further treated or functionalized; and b) applying a sensing element to the paper substrate, the sensing element (Continued)

selected from the group consisting of a conductive material, the conductive material providing contacts and interconnects, sensitive material film that exhibits sensitivity to pH levels, a compressible and/or porous material disposed between a pair of opposed conductive elements, or a combination of two of more said sensing elements. The method of sensing can further include measuring, using the sensing element, a change in resistance, a change in voltage, a change in current, a change in capacitance, or a combination of any two or more thereof.

20 Claims, 27 Drawing Sheets

(51) Int. Cl.
| | | |
|---|---|---|
| G01N 27/22 | (2006.01) | |
| H03K 17/96 | (2006.01) | |
| B01L 3/00 | (2006.01) | |
| G01L 1/14 | (2006.01) | |
| G01D 21/00 | (2006.01) | |
| H03K 17/955 | (2006.01) | |
| B81C 1/00 | (2006.01) | |
| A61B 5/021 | (2006.01) | |
| A61B 5/024 | (2006.01) | |
| A61B 5/08 | (2006.01) | |
| A61B 5/145 | (2006.01) | |
| A61B 5/00 | (2006.01) | |
| G01L 1/20 | (2006.01) | |
| G01N 27/12 | (2006.01) | |

(52) U.S. Cl.
CPC ........ *A61B 5/02444* (2013.01); *A61B 5/0816* (2013.01); *A61B 5/14539* (2013.01); *A61B 5/4266* (2013.01); *A61B 5/445* (2013.01); *B01L 3/502707* (2013.01); *B81C 1/00166* (2013.01); *G01D 21/00* (2013.01); *G01L 1/142* (2013.01); *G01L 1/20* (2013.01); *G01N 27/125* (2013.01); *G01N 27/223* (2013.01); *H03K 17/955* (2013.01); *H03K 17/962* (2013.01); *A61B 2562/028* (2013.01); *A61B 2562/029* (2013.01); *A61B 2562/0219* (2013.01); *A61B 2562/0247* (2013.01); *A61B 2562/0257* (2013.01); *A61B 2562/0271* (2013.01); *A61B 2562/125* (2013.01); *B01L 2300/0663* (2013.01); *B01L 2300/126* (2013.01); *B01L 2400/0406* (2013.01); *B81B 2201/0214* (2013.01); *B81B 2201/0264* (2013.01); *B81B 2201/0278* (2013.01); *G01N 27/12* (2013.01); *H03K 2217/960755* (2013.01)

(58) Field of Classification Search
CPC ...... B01L 2300/126; G01L 1/142; G01L 1/20; H03K 17/955; H03K 17/962; H03K 2217/960755; B81C 1/00166; A61B 5/02141; A61B 5/02444; A61B 5/0816; A61B 5/14539; A61B 5/4266; A61B 5/445; A61B 5/01; A61B 2562/029; A61B 2562/0219; A61B 2562/0247; A61B 2562/0271; A61B 2562/125; A61B 2562/0257; A61B 2562/028; G01N 27/125; G01N 27/223; G01N 27/12; B81B 2201/0264; B81B 2201/0278; B81B 2201/0214
USPC ................ 324/693, 691, 649, 600
See application file for complete search history.

(56) References Cited

U.S. PATENT DOCUMENTS

| | | | |
|---|---|---|---|
| 2013/0053669 A1* | 2/2013 | Yoo ................. | A61B 5/04 600/372 |
| 2014/0154788 A1 | 6/2014 | Omenetto et al. | |
| 2014/0210479 A1* | 7/2014 | Rink ................. | G01R 1/203 324/426 |
| 2014/0224018 A1 | 8/2014 | Whitesides et al. | |
| 2015/0114850 A1* | 4/2015 | Prasad ............... | G01N 27/026 205/792 |
| 2015/0126834 A1* | 5/2015 | Wang ................ | B32B 38/145 600/345 |
| 2016/0051980 A1* | 2/2016 | Hong ................ | B01L 3/5023 506/39 |
| 2017/0128008 A1* | 5/2017 | Chung ............... | A61B 5/6804 |
| 2020/0064323 A1* | 2/2020 | Doshi ............... | G01N 27/228 |

OTHER PUBLICATIONS

Lu, M., et al., "Voltammetric pH Sensing Using Carbon Electrodes: Glassy Carbon Behaves Similarly to EPPG," Analyst, The Royal Society of Chemistry, Jul. 9, 2014, vol. 139, pp. 4599-4605.
Mraović, M., et al., "Humidity Sensors Printed on Recycled Paper and Cardboard," Sensors, Jul. 28, 2014, vol. 14, pp. 13628-13643.
Dinh, T., et al., "Graphite on Paper as Material for Sensitive Thermoresistive Sensors," Journal of Materials Chemistry C, Jul. 15, 2015, vol. 3, pp. 8776-8779.
Written Opinion of the International Searching Authority in related International Application No. PCT/IB2017/050202, dated May 4, 2017.
Abdullah, S.M., et al., "A Solution-Based Temperature Sensor Using the Organic Compound CuTsPc," Sensors, vol. 14, Jun. 4, 2014, pp. 9878-9888.
Agilent Technologies, "Linear Thermal Expansion Coefficients of Metals and Alloys," Laser and Optics User's Manual, Chapter 17—Material Expansion Coefficients, Jul. 2002, pp. 17-1-17-12.
Arumugam, V., et al., "Effect of strain rate on the fracture behaviour of skin," J. Biosci., vol. 19, No. 3, Sep. 1994, pp. 307-313.
Balasubramanian, N., "Relative merits of Polyester and Polypropylene," asp 2015, 2 pages, http://www.fibre2fashion.com/industryarticle/textile-industry-articles/polyester-vs-polypropylene/polyester-vs-polypropylene1.
Celin, S., et al., "Survey on the Methods for Detecting Arrhythmias Using Heart Rate Signals," Journal of Pharmaceutical Sciences and Research, vol. 9, No. 2, Feb. 2017, pp. 183-189.
Chung, V.P.J., et al., "A CMOS Capacitive Vertical-Parallel-Plate-Array Humidity Sensor With RF-Aerogel Fill-in for Sensitivity and Response Time Improvement," MEMS 2015, Estoril, Portugal, Jan. 18-22, 2015, pp. 767-770.
Cotton, D.P.J., et al., "A Multifunctional Capacitive Sensor for Stretchable Electronic Skins," IEEE Sensors Journal, vol. 9, No. 12, Dec. 2009 (Current Version published Nov. 4, 2009), pp. 2008-2009.
Fantin, F., et al., "Is augmentation index a good measure of vascular stiffness in the elderly?", Age and Ageing, vol. 36, 2007 (Published electronically Nov. 17, 2006), pp. 43-48.
Gao, L., et al., "Epidermal photonic devices for quantitative imaging of temperature and thermal transport characteristics of the skin," Nature Communications, vol. 5, Article 4938, Sep. 19, 2014, pp. 1-10.
Gu, L., et al., "A novel capacitive-type humidity sensor using CMOS fabrication technology," Sensors and Actuators B: Chemical, vol. 99, Issues 2-3, May 2004, pp. 491-498.
Hammock, M.L, et al., "25th Anniversary Article: The Evolution of Electronic Skin (E-Skin): A Brief History, Design Considerations, and Recent Progress," Advanced Materials, vol. 25, 2013 (Published online Oct. 22, 2013), pp. 5997-6038.
Han, J.-W., et al., "A carbon nanotube based ammonia sensor on cellulose paper," RSC Advances, vol. 4, 2014 (Published Nov. 22, 2013), pp. 549-553.

(56) References Cited

OTHER PUBLICATIONS

Han, J.-W., et al., "Carbon Nanotube Based Humidity Sensor on Cellulose Paper," The Journal of Physical Chemistry C, vol. 116, Sep. 25, 2012, pp. 22094-22097.

Harada, S. et al., "Fully Printed Flexible Fingerprint-like Three-Axis Tactile and Slip Force and Temperature Sensors for Artificial Skin," ACS Nano, vol. 8, No. 12, 2014 (Published online Dec. 1, 2014), pp. 12851-12857.

Hizawa, T., et al., "Fabrication of a two-dimensional pH image sensor using a charge transfer technique," Sensors and Actuators B: Chemical, vol. 117, 2006 (Available online Mar. 22, 2006), pp. 509-515.

Huang, X. et al., "Materials and Designs for Wireless Epidermal Sensors of Hydration and Strain," Advanced Functional Materials, vol. 24, 2014 (Published online Mar. 2, 2014), pp. 3846-3854.

Jang, J., et al., "Fabrication of Water-Dispersible Polyaniline-Poly(4-styrenesulfonate) Nanoparticles for Inkjet-Printed Chemical-Sensor Applications," Advanced Materials, vol. 19, Issue 13, 2007 (First published Jun. 26, 2007), pp. 1772-1775.

Jung, S., et al., "Reverse-Micelle-Induced Porous Pressure-Sensitive Rubber for Wearable Human-Machine Interfaces," Advanced Materials, vol. 26, 2014 (Published online May 15, 2014), pp. 4825-4830.

Kim, J., et al., "Stretchable silicon nanoribbon electronics for skin prosthesis," Nature Communications, vol. 5, Article 5747, Dec. 9, 2014, pp. 1-11.

Kimberly-Clark Professional, "Kimtech Science Kimwipes," 2013, 2 pages, http://kcprofessional.com/products/wipers/specialty/kimtech-science/34120-kimtech-science-kimwipes-delicate-task-wipers.

Koga, H., et al., "Uniformly connected conductive networks on cellulose nanofiber paper for transparent paper electronics," NPG Asia Materials, vol. 6, 2014 (Published online Mar. 21, 2014), pp. 1-8.

Kozub, B.R., et al., "Voltammetric studies of the redox mediator, cobalt phthalocyanine, with regard to its claimed electrocatalytic properties," Sensors and Actuators B: Chemical, vol. 147, 2010 (Available online Mar. 6, 2010), pp. 350-358.

Lakafosis, V., et al., "Progress Towards the First Wireless Sensor Networks Consisting of Inkjet-Printed, Paper-Based RFID-Enabled Sensor Tags," Proceedings of the IEEE, vol. 98, No. 9, Sep. 2010 (Manuscript published Jul. 1, 2010), pp. 1601-1609 (10 pages provided).

Lee, C.-Y., et al., "Embedded flexible micro-sensors in MEA for measuring temperature and humidity in a micro-fuel cell," Journal of Power Sources, vol. 181, 2008 (Available online Jan. 17, 2008), pp. 237-243.

Lei, N., et al., "Simple graphene chemiresistors as pH sensors: fabrication and characterization," Measurement Science and Technology, vol. 22, 2011 (Published online Aug. 26, 2011), pp. 1-6 (7 pages provided).

Lessing, J., et al., "Inkjet Printing of Conductive Inks with High Lateral Resolution on Omniphobic "RF Paper" for Paper-Based Electronics and MEMS," Advanced Materials, vol. 26, 2014 (Published online May 30, 2014), pp. 4677-4682.

Lin, C.-H., et al., "MEMS-based Humidity Sensor Based on Thiol-coated Gold Nanoparticles," Proceedings of the 9th IEEE International Conference on Nano/Micro Engineered and Molecular Systems, Hawaii, USA, Apr. 13-16, 2014, pp. 191-194.

Lipomi, D.J., et al., "Skin-like pressure and strain sensors based on transparent elastic films of carbon nanotubes," Nature Nanotechnology, vol. 6, Dec. 2011 (Published online Oct. 23, 2011), pp. 788-792.

Liu, X., et al., "A highly sensitive pressure sensor using a Au-patterned polydimethylsiloxane membrane for biosensing applications," Journal of Micromechanics and Microengineering, vol. 23, 2013 (Published online Jan. 21, 2013), pp. 1-10 (12 pages provided).

Manzoli, A., et al., "Low-Cost Gas Sensors Produced by the Graphite Line-Patterning Technique Applied to Monitoring Banana Ripeness," Sensors, vol. 11, Jun. 17, 2011, pp. 6425-6434.

Marwick, T.H., et al., "Recommendations on the Use of Echocardiography in Adult Hypertension: A Report from the European Association of Cardiovascular Imaging (EACVI) and the American Society of Echocardiography (ASE)," Journal of the American Society of Echocardiography, vol. 28, No. 7, Jul. 2015, pp. 727-754.

Mole, R.H., "The Relative Humidity of the Skin," J. Physiol., vol. 107, 1948 (First Published Sep. 30, 1948), pp. 399-411.

Mürtz, P., et al., "LMR spectroscopy: a new sensitive method for on-line recording of nitric oxide in breath," J. Appl. Physiol., vol. 86, No. 3, 1999 (Published online Mar. 1, 1999), pp. 1075-1080.

Muxfeldt, E.S., et al., "Ambulatory Arterial Stiffness Index or Pulse Pressure: Which Correlates Better with Arterial Stiffness in Resistant Hypertension?", Hypertens. Res., vol. 31, No. 4, Apr. 2008, pp. 607-613.

Nave, C.R., "Resistor Temperature Dependence," HyperPhysics, Temperature Coefficient of Resistance, 2001, 3 pages, http://hyperphysics.phyastr.gsu.edu/hbase/electric/restmp.html.

Park, S., et al., "Stretchable Energy-Harvesting Tactile Electronic Skin Capable of Differentiating Multiple Mechanical Stimuli Modes," Advanced Materials, vol. 26, 2014 (Published online Sep. 25, 2014), pp. 7324-7332.

Queensland Curriculum & Assessment Authority, "Extended experimental investigation: Electrical conductivity of graphite," Queensland Studies Authority, Physics (2007): Sample assessment instrument and student response, Jun. 2013, pp. 1-11, https://www.qcaa.qld.edu.au/downloads.senior/snr_physics_07_sai_electric_conduct_graphite.pdf.

Ramuz, M., et al., "Transparent, Optical, Pressure-Sensitive Artificial Skin for Large-Area Stretchable Electronics," Advanced Materials, vol. 24, 2012 (Published online May 29, 2012), pp. 3223-3227.

Russo, A., et al., "Pen-on-Paper Flexible Electronics," Advanced Materials, vol. 23, 2011 (Published online Jun. 20, 2011), pp. 3426-3430.

Schwartz, G., et al., "Flexible polymer transistors with high pressure sensitivity for application in electronic skin and health monitoring," Nature Communications, vol. 4, Article 1859, May 14, 2013, pp. 1-8.

Segev-Bar, M., et al., "Tunable Touch Sensor and Combined Sensing Platform: Toward Nanoparticle-based Electronic Skin," ACS Applied Materials & Interfaces, vol. 5, Jun. 4, 2013, pp. 5531-5541.

Sekitani, T., et al., "Stretchable, Large-area Organic Electronics," Advanced Materials, vol. 22, 2010 (Published online Mar. 12, 2010), pp. 2228-2246.

Sheppard, Jr., N.F., et al., "Microfabricated conductimetric pH sensor," Sensors and Actuators B: Chemical, vol. 28, Issue 2, Aug. 1995, pp. 95-102.

Siegel, A.C., et al., "Thin, lightweight, foldable thermochromic displays on paper," Lab on a Chip, vol. 9, No. 19, Oct. 7, 2009 (Published on the web Jun. 23, 2009), pp. 2775-2781.

Someya, T., "Building Bionic Skin: How flexible electronics can provide e-skins for humans," North American, Spectrum.IEEE.Org, Sep. 2013, pp. 51-56 (7 pages provided).

Someya, T., et al., "Conformable, flexible, large-area networks of pressure and thermal sensors with organic transistor active matrixes," PNAS, vol. 102, No. 35, Aug. 30, 2005, pp. 12321-12325.

Sun, J.-Y., et al., "Ionic Skin," Advanced Materials, vol. 26, 2014 (Published online Oct. 29, 2014), pp. 7608-7614.

Takahashi, T., et al., "Carbon Nanotube Active-Matrix Backplanes for Conformal Electronics and Sensors," Nano Letters, vol. 11, Nov. 3, 2011, pp. 5408-5413.

Takei, K., et al., "Nanowire active-matrix circuitry for low-voltage macroscale artificial skin," Nature Materials, vol. 9, Oct. 2010 (Published online Sep. 12, 2010), pp. 821-826.

Tan, E.L., et al., "A Wireless, Passive Sensor for Quantifying Packaged Food Quality," Sensors, vol. 7, Sep. 5, 2007, pp. 1747-1756.

Tien, N.T., et al., "A Flexible Bimodal Sensor Array for Simultaneous Sensing of Pressure and Temperature," Advanced Materials, vol. 26, 2014 (Published online Oct. 23, 2013), pp. 796-804.

(56) References Cited

OTHER PUBLICATIONS

Tobjörk, D., et al., "Paper Electronics," vol. 23, 2011 (Published online Mar. 23, 2011), pp. 1935-1961.

Tomizuka, C.T., et al., "Self-Diffusion in Silver," Physical Review, vol. 103, No. 5, Sep. 1, 1956, pp. 1182-1184.

Unander, T., et al., "Characterization of Printed Moisture Sensors in Packaging Surveillance Applications," IEEE Sensors Journal, vol. 9, No. 8, Aug. 2009 (Published Jun. 26, 2009), pp. 922-928.

Wang, C., et al., "User-interactive electronic skin for instantaneous pressure visualization," Nature Materials, vol. 12, Oct. 2013 (Published online Jul. 21, 2013), pp. 899-904.

Wang, L., et al., "Simple, Rapid, Sensitive, and Versatile SWNT-Paper Sensor for Environmental Toxin Detection Competitive with ELISA," Nano Letters, vol. 9, No. 12, 2009 (Published on the web Nov. 20, 2009), pp. 4147-4152.

Wang, X., et al., "Silk-Molded Flexible, Ultrasensitive, and Highly Stable Electronic Skin for Monitoring Human Physiological Signals," Advanced Materials, vol. 26, 2014 (Published online Dec. 17, 2013), pp. 1336-1342.

Yamazoe, N., et al., "Humidity Sensors Principles and Applications," Sensors and Actuators, vol. 10, Nov.-Dec. 1986, pp. 379-398.

Yang, T., et al., "Fabrication of silver interdigitated electrodes on polyimide films via surface modification and ion-exchange technique and its flexible humidity sensor application," Sensors and Actuators B: Chemical, vol. 208, 2015 (Available online Nov. 15, 2014), pp. 327-333.

Yun, S., et al., "Multi-walled carbon nanotubes-cellulose paper for a chemical vapor sensor," Sensors and Actuators B: Chemical, vol. 150, 2010 (Available online Jul. 8, 2010), pp. 308-313.

Zang, Y., et al., "Flexible suspended gate organic thin-film transistors for ultra-sensitive pressure detection," Nature Communications, vol. 6, Article 6269, Mar. 3, 2015, pp. 1-9.

\* cited by examiner

(d) Pressure sensor design 1

(e) Pressure sensor design 2

FIG. 3(a)
FIG. 3(b)
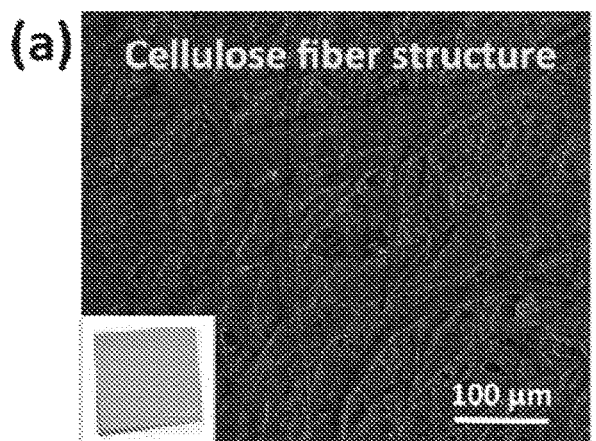
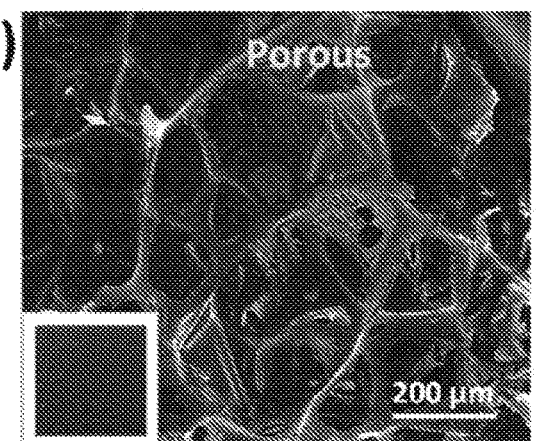
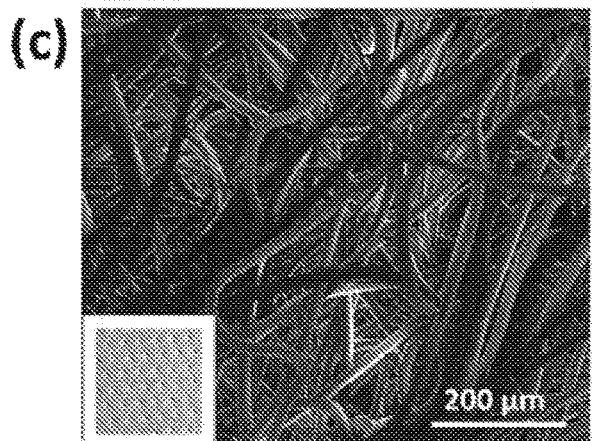
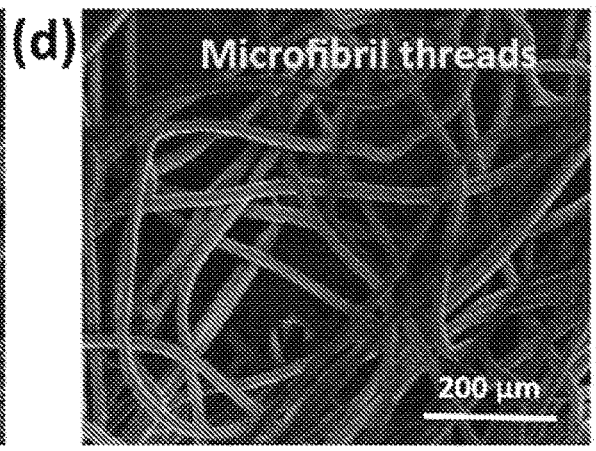
FIG. 3(c)
FIG. 3(d)

(g)

(h)

PAPER BASED ELECTRONICS PLATFORM

CROSS-REFERENCE TO RELATED APPLICATIONS

This application is a U.S. National Stage Application of International Application No. PCT/IB2017/050202, filed on Jan. 13, 2017, which claims the benefit of and priority to U.S. Provisional Application Ser. No. 62/278,545, having the title "PAPER BASED ELECTRONICS PLATFORM," filed on Jan. 14, 2016, the disclosures of which are incorporated herein by reference in their entirety.

TECHNICAL FIELD

The present disclosure generally relates to paper based electronics.

BACKGROUND

Paper is a universally widespread material that is available in every household due to its low-cost and necessity for everyday use. One of the advantages of using paper substrates for sensors applications is its porosity and its larger interfacial area that promotes both high sensitivity and fast response. To date, several works have used paper as a host platform or a sensing material for building various types of devices, ranging from flexible actuators to displays and paper-based MEMS electronics[1-6]. Advancements in the field of paper electronics are rapidly growing, where major focus has been directed toward using flexible cellulose paper for the fabrication of various types of sensors, such as humidity, touch, pH, and gas sensors[7-10]. However, these approaches still use sophisticated and often expensive nanomaterials based functionalization, vacuum manufacturing processes and printing techniques, where paper is still often chemically treated and solution-processed[11-13].

Flexible artificial skin advances have also paved their way in the literature, aiming for soft skins for robotic applications through the means of pressure and temperature sensors integrated on polyethylene terephthalate (PET) or polyimide (PI) substrates[14-19]. However, the existing approaches are still far from being commercialized due to their fairly expensive manufacturing processes and complex integration. Although flexible plastic substrates are relatively cheap (PET$\approx$2 cents.dm$^{-2}$ & PI$\approx$30 cents.dm$^{-2}$ \), the price of paper is substantially lower ($\approx$0.1 cent.dm$^{-2}$)[6]. Developments in artificial skin integration have shown possibilities for strain, humidity, pressure and temperature sensing[20-31]. There continues to be a need, however, for cheaper alternatives.

SUMMARY

We provide a flexible and non-functionalized low cost electronic system platform fabricated from common paper. In various aspects we display both in-plane and 3D-integration of various sensors for health monitoring, for example, for real-time monitoring of temperature, sweat, burn effect, breathing, heart rate and blood pressure. Additionally we show computational, radio communication, light steering and lasing ability.

We provide herein a cheaper alternative to the widespread artificial skin systems. In various aspects, we provide paper-based sensors employing common fabrication tools in which we do not functionalize or treat the paper in any way, nor use any microfabrication processes such as sputtering, shadow mask, or solution etching techniques. Our fabrication process allows for household manufacturing of the sensors, making them accessible for anyone, at any age and regardless of financial status.

In various aspects, we provide a 3D stacked "Paper Skin" array (for example a 6×6 array) for simultaneous sensing. The array can be manufactured from household resources such as paper, 3M™ adhesive tape, aluminum/copper foil, kitchen sponge, tissue fabric (napkins), and pencil. Although aluminum foil is sufficient for interconnects and contacting pads, we can also use, for example, a silver conducive ink, such as the silver conductive ink pen "Circuit Scribe"[32], for scalability and arraying purposes. We can use off-the-shelf materials to fabricate and integrate the sensors such as pressure, temperature, humidity, pH, and flow sensors including tactile and proximity detection.

Unlike artificial skin platforms aiming for high-end sensitivities, in an aspect we disclose herein a low-cost and multi-functional paper-based sensors network providing sufficient functionality and ease of access to monitoring and awareness systems. The ability to capture pressure, tactile, proximity and motion positions unexpectedly enables more intuitive human-computer interactions, in a much more accessible way than before. Our "paper skin" can be employed in various household and healthcare applications, ranging from food quality examination, to atmospheric monitoring, and basic real-time symptoms and illness detection.

In an embodiment, a method of producing a paper based sensor is provided. The method can comprise the steps of: a) providing a conventional paper product to serve as a substrate for the sensor or as an active material for the sensor or both, the paper product not further treated or functionalized; and b) applying a sensing element to the paper substrate, the sensing element selected from the group consisting of a conductive material, the conductive material providing contacts and interconnects, sensitive material film that exhibits sensitivity to pH levels, a compressive and/or porous material disposed between a pair of opposed conductive elements, or a combination of two of more said sensing elements.

In any one or more aspects of the method the conventional paper product can be selected from the group consisting of cellulose fiber based porous structures. The sensing element can be a temperature sensor, humidity sensor, pH sensor, gas sensor, pressure/force sensor, tactile sensor, proximity sensor and/or a combination of two or more of said sensors. The sensing element can be made using a metal foil, a conductive ink, material that exhibits an amount of compressibility, a microfiber wipe, a sponge, a graphite composition, or a combination thereof. The sensor can be either a temperature sensor or a humidity sensor and the sensing element can be formed of a metal foil or a conductive ink or both. The sensor can be a pH sensor and the sensitive material that exhibits sensitivity to pH can be formed of a graphite composition. The sensor can be a pressure/tactile sensor and the sensing element can be formed of a pair of conductive elements and a material that exhibits an amount of compressibility (for example a microfiber fabric or a sponge material) disposed between the pair of conductive elements. The sensor can be formed of an array of temperature sensors, humidity sensors and pressure sensors stacked, the arrays stacked one on top of the other on the paper substrate.

In an embodiment a method of sensing is provided. The method can comprise the steps of: a) providing a conventional paper product to serve as a substrate for the sensing or as an active material for the sensing, the paper product not further treated or functionalized; b) applying a sensing element to the paper substrate, the sensing element selected from the group consisting of any kind of conductive material serving as contacts and interconnects, any kind of sensitive material films that exhibit sensitivity to pH levels, a compressive and/or porous material disposed between a pair of opposed conductive elements, or a combination of two of more said sensing elements; c) and measuring, using the sensing element, a change in resistance, a change in voltage, a change in current, a change in capacitance, or a combination of any two or more thereof.

In any one or more aspects of the method of sensing the conventional paper product can be selected from the group consisting of cellulose fiber based porous structures. The sensing element can create a sensor, such as a temperature sensor, a humidity sensor, pH sensor, gas sensor, pressure/force sensor, a tactile sensor, a proximity sensor, or a combination of two or more of said sensors. The sensing element can be formed of a metal foil, a conductive ink, a material that exhibits an amount of compressibility, a microfiber wipe, a sponge, a graphite composition, or a combination thereof. The conductive material can be selected from the group consisting of a metal foil or a conductive ink. The sensitive material that exhibits sensitivity to pH can be a graphite composition, The sensing element can form either a temperature sensor or a humidity sensor and the sensing element can be formed of a metal foil or a conductive ink or both. The sensing element can form a pH sensor and the sensing element can be formed of a graphite composition. The sensing element can form a pressure/tactile sensor and the sensing element can be formed of pair of conductive elements and a material that exhibits an amount of compressibility (such as a microfiber fabric or a sponge material) disposed between the pair of conductive elements. The sensing element can form an array of temperature sensors, humidity sensors and pressure/force/tactile/proximity sensors stacked, the arrays stacked one on top of the other on the paper substrate or integrated in a plane.

In an embodiment, a paper based sensor is provided. The paper based sensor can comprise: 1) a conventional paper product to serve as a substrate for the sensor or as an active material for the sensor or both, the conventional paper product not further treated or functionalized: and b) a sensing element on or applied to the paper substrate, the sensing element selected from the group consisting of a conductive material, the conductive material providing contacts and interconnects, sensitive material film that exhibits sensitivity to pH levels, a compressible and/or porous material disposed between a pair of opposed conductive elements, or a combination of two of more said sensing elements.

In any one or more aspects of the paper based sensor, the conventional paper product can be selected from the group consisting of cellulose fiber based porous structures. The sensing element can be a temperature sensor, humidity sensor, pH sensor, gas sensor, pressure/force sensor, tactile sensor, proximity sensor and/or a combination of two or more of said sensors. The sensing element can be made using a metal foil, a conductive ink, material that exhibits an amount of compressibility, a microfiber wipe, a sponge, a graphite composition, or a combination thereof. The sensor can be either a temperature sensor or a humidity sensor and the sensing element can be formed of a metal foil or a conductive ink or both. The sensor can be a pH sensor and the sensitive material that exhibits sensitivity to pH formed of a graphite composition. The sensor can be a pressure/tactile sensor and the sensing element formed of pair of conductive elements and a microfiber fabric or a sponge material disposed between the pair of conductive elements. The sensor can be formed of an array of temperature sensors, humidity sensors and pressure sensors stacked, the arrays stacked one on top of the other on the paper substrate.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1(a) is a schematic of temperature sensors using silver ink pen and aluminum foil; FIG. 1(b) shows a capacitive design of humidity sensor using Post-it™ paper as sensing material; FIG. 1(c) depicts a representative capacitive based disposable pH sensor; FIG. 1(d) depicts a pressure sensor using a parallel-plate structure and two different sensing materials; microfiber wipe and a sponge; and FIG. 1(e) depicts a schematic of a second pressure sensor design based on an air-gap structure.

FIGS. 2(a)-(d) depict a sensor array: in which FIG. 2(a) shows a flexible paper skin; FIG. 2(b) a flexible 6×6 "Paper Skin" wrapped around an arm; FIG. 2(c) a schematic of a 3D stacked paper skin structure composed of pressure, temperature and humidity sensors; and FIG. 2(d) a schematic of an in-plane integration of paper skin with inset zoomed on 2 pixels configuration.

FIGS. 3(a)-(d) depict structural material properties of household resources: in which FIG. 3(a) is scanning electron microscopy (SEM) of Post-it™ paper coated with 2 nm Iridium (Ir) reflecting the porosity of the paper through its cellulose fiber structure; FIG. 3(b) is an SEM image of the foamed polyester sponge highlighting its porous and deformable nature through a system of hexagonal microstructures; and FIGS. 3(c) and 3(d) are SEM images of the cleanroom wipe, displaying randomly oriented microfibril threads with varying densities across the film.

FIGS. 4(a)-(f) depict material properties of silver (Ag) ink pen on Post-it™ paper: in which FIGS. 4(a), (b), and (c) are scanning electron microscopy (SEM) of silver ink on paper, at room temperature (T=25° C.). The zoomed-in images show the uniform distribution of distinct Ag hexagonal microstructures, with slight separation in between; and FIGS. 4(d), (e), and (f) are SEM images of the same silver ink structure after heating at 100° C. and left to cool down at room temperature. The Ag microstructures have expanded and superimposed, yielding to a much denser and uniform film.

FIG. 6(a) shows temperature sensitivity of an aluminum foil-based sensor, displaying a sensitivity of 0.00115Ω/° C.

FIGS. 7(a)-(c) depict real-time temperature monitoring: in which FIG. 7(a) shows total response and recovery times due to human touch stimulus; FIG. 7(b) shows spike response time originating from human breath heat; and FIG. 7(c) shows peak response behavior with fast response time to flame temperature.

FIGS. 8(a)-(i) depict single pixel real-time temperature and humidity sensing: in which FIG. 8(a) is a digital photograph showing external stimuli from human touch, exerting a temperature of around T=37° C.; FIG. 8(b) shows a real-time temperature response to human touch, displaying a Gaussian/Lorentzian profile for 3 consecutive cycles; FIG. 8(c) is a digital photo showing external stimuli from human exhaled breath (around 42° C.); FIG. 8(d) is a real-time temperature response for 2 cycles of exhaled breath over a period of 30 seconds; FIG. 8(e) is a digital photo showing external stimulus exerted from the flame of a lighter (T=85° C.), positioned 10 cm away from the surface of the sensor; FIG. 8(f) shows a real-time response for 5 cycles of applied stimuli over a period of 80 seconds; FIG. 8(g) shows a real-time response to humidity levels detected from 4 cycles of human breath; Fig. (h) is a real-time humidity profile showing a null response to the fan breeze (reference plot), and a positive response due to water vapor detection; and FIG. 8(i) is a digital photo illustrating the wind tunnel setup used to properly redirect the vapor on top of the humidity sensor.

FIGS. 9(a)-(d) depict real-time humidity monitoring: in which FIG. 9(a) is a sensitivity plot displaying linear change in capacitance as humidity levels increase; FIG. 9(b) shows peak response displaying an exponential increase in capacitance with detected breath humidity; FIG. 9(c) is a response profile due to water vapor humidity detection; and FIG. 9(d) is a photograph demonstrating the experimental setup for applying water vapor on the surface of the humidity sensor.

FIGS. 10(a)-(i) depict pH and real-time pressure measurements: in which FIG. 10(a) shows a study of pH sensor behavior using 2 mL of coffee, water, and backing soda solutions; FIG. 10(b) shows a comparative study of pressure-sensing behaviors between cleanroom wipe and sponge; FIG. 10(c) is a C-V measurement of an air-gap based pressure sensor, under various pressure loads; FIG. 10(d) is a sensing behavior plot of an air-gap pressure sensor (scale bar of inset digital photo is 3 cm); FIG. 10(e) shows a real-time capacitance change in response to applied 12 kPa, exerted with the bottom of a pen (scale bar of inset digital photo is 1 cm); FIG. 10(f) shows a peak behavior in response to 12 kPa load; FIG. 10(g) shows a real-time sensing of 32 touch-release cycles within a time of 50 s (Scale bar of inset digital photo is 1 cm); and FIG. 10(h) shows a mutual capacitance effect in response to touch; and FIG. 10(i) shows a systolic pressure response when finger touch is pressed further against the sensor.

FIGS. 11(a)-(c) depict real-time pressure flow monitoring: in which FIG. 11(a) shows pressure behavior to airflow at an applied normal velocity of $v_{normal}$=3 m/s; FIG. 11(b) shows pressure response to different flow orientations (0°, 45° and 90°), for two velocity values: 2 m/s and 8 m/s; and FIG. 11(c) is a pressure sensitivity plot at fixed flow velocities.

FIGS. 12(a) and (b) depict out-of-plane proximity sensing: in which FIG. 12(a) shows real-time monitoring of out-of plane proximity sensing, where the finger approaches the sensor in a perpendicular manner (proximity sensing detected at 13 cm away from the sensor); and FIG. 12(b) shows capacitance decreases exponentially as the finger gradually approaches the sensor. Scale bar of inset digital photos is 2 cm.

FIGS. 13(a)-(h) depict a "Paper Skin" spatial and temporal mapping: in which FIG. 13(a) shows a temperature array pixel distribution, showing Pixel R1-C1 damaged; FIG. 13(b) is a spatial mapping of temperature generated from human touch exerted on pixels R3-C3 and R5-C6; FIG. 13(c) shows a humidity array pixel-to-pixel uniformity; FIG. 13(d) is a spatial mapping of humidity in response to human breath exerted simultaneously on pixels R2-C3, R2-C4, R3-C2, R3-C5, R4-C2, R4-C5, R5-C3, and R5-C4; FIG. 13(e) shows a pressure array pixel uniformity; FIG. 13(f) shows a spatial mapping of pressure in a "Chessboard" pattern; FIG. 13(g) is a 3D bars representation corresponding to localized 8 kPa loads on pixels R1-C2 and R6-C5; and FIG. 13(h) is a simultaneous temporal and spatial mapping of motion sensing from 4 pixels.

FIGS. 14(a)-(h) depict simultaneous body vitals monitoring: in which FIG. 14(a) is a digital photo showing a setup for heart rate monitoring by carefully taping the paper skin on the chest; FIG. 14(b) is a heart rate pressure profile before exercise, with comparative digital photo inset taken from Samsung S5 "S Health" application; FIG. 14(c) shows a heat rate detection after exercise, with inset from "S Health" monitoring application; FIG. 14(d) is a digital photo showing paper skin wrapped around the wrist for complete body vitals detection; FIG. 14(e) is a radial artery pulse waveform detected throughout a period of 30 s, and band pass filtered between 1 and 7 Hz for noise elimination; FIG. 14(f) shows a heart rate detection from arterial pulse monitoring; FIG. 14(g) shows blood pressure and arterial stiffness detection from resolvable peaks of the radial artery waveform; and FIG. 14(h) is a histogram displaying simultaneous sensing of body temperature and skin humidity before and after exercise.

DETAILED DESCRIPTION

Figure 1A:
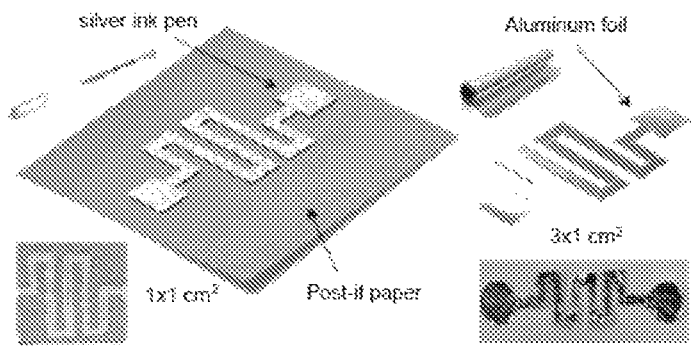
FIGS. 1(a)-(e) depict a fabrication process of various paper sensors of the present disclosure.

Described below are various embodiments of the present systems and methods for a paper based electronics platform. Although particular embodiments or examples are described, they are mere exemplary implementations of the system and method. One skilled in the art will recognize other embodiments are possible, All such embodiments or examples are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiments disclosed herein. On the contrary, the intent is to cover all alternatives, modifications and equivalents included within the spirit and scope of the disclosure.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic inorganic chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar. However, we may use pressure units in the form of Pa or kPa.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Description

In an embodiment, we provide various electronics platforms using paper as a substrate. In various aspects the paper can be selected from cellulose fiber based porous structures. The paper can be any conventional or commonly available paper, such as household paper, and can be generalized to any kind of cellulose fiber based paper. The paper can be a commercially available paper, such as Post-it® Notes, stationary paper, all-purpose papers used in printing or for documents, business cards, envelopes, magazines, etc. The paper does not need to be further treated or functionalized for use herein. The paper does not need to be treated or functionalized beyond the condition of the conventional or commonly available paper as received or purchased, Paper as commonly produced can be used herein without being subjected to treatment or functionalization subsequent to its production. Thus, for example, it is not necessary to impregnate the as received paper, such as by application of an emulsion, or to coat the paper for use herein. In any one or more aspects, the paper can be an untreated paper by which we mean a paper having an untreated surface that is dull and unreflective. In any one or more aspects, an untreated paper as used herein can be a conventional or commonly available as received paper that has not been subjected to a treatment to impregnate the paper or subject the operative surface of the paper to coating or varnish treatment. In any one or more aspects, the as received paper is an untreated paper in the form of a thin fibrous sheet laid down from a suspension of pulped fibers (typically cellulosic fibers) which may contain various amounts of non-fibrous ingredients, such as in a conventional paper-making process.

Characteristics that can affect from the choice of paper used are its porosity and surface roughness. These parameters can affect the uniformity of the metal interconnects and the sensitivity of the humidity sensor. However, our sensors integration is not limited to the choice of the paper type. Any paper platform can be used for fully functional sensors, and changes in the paper type will only result in changes in the sensitivities of the sensors built on it. The paper can provide a flexible substrate for the platform. Other characteristics of the paper such as porosity and cellulose and fiber structure do not restrict most the sensors functionality, except for humidity sensing, where porosity of the paper can affect the sensitivity and response time of the sensor, but does not restrict the functioning of the sensor. The paper-based platform can provide various sensor designs.

A metal foil (such as aluminum foil) or a conductive ink (such as a metallic ink, for example a silver ink) can be used for the contact pads and interconnects of the sensor. A spectrum of materials and structures can be used for the sensing film in order to achieve the desired performance and application. Table 1 provides a list of some materials that can be used for various sensors of the present disclosure, highlighting their important characteristics.

TABLE 1

Household material properties

| Household Resources | Purpose of use | Thickness | Relative permittivity ($\epsilon_r$) | Electrical Resistivity ($\rho$) |
|---|---|---|---|---|
| 3M Post-it™ Note | Substrate; humidity sensing film | 100 μm | 19.8 | — |
| Aluminum Foil | Contacts; interconnects | 15 μm | — | $3.83 \times 10^{-8}$ Ω·m |
| Conductive Silver Pen (CircuitScribe™) | Contacts; interconnects | — | — | 0.05-0.2 ohms/sq |
| Microfiber Wipe | Pressure sensing film | 600 μm | 4.09 | — |
| Sponge | Pressure sensing film | 0.7 cm | 13.5 | — |
| Kimtech™ Wipe | Protective film for humidity sensor | 60 μm | 1.88 | — |
| Double-sided adhesive Tape | Adhesive; dielectric material | 90 μm | 2.1 | — |
| HB pencil | PH sensing film | — | — | $1.85 \times 10^{-4}$ Ω·m |

In various aspects, our paper-based electronics platform can show any kind of sensor functionality, including but not restricted to, temperature sensors, a humidity sensors, pH sensors, pressure/tactile sensors, proximity sensors and combinations thereof. Both temperature and pH sensors have a resistive functionality, whereas humidity and pressure/tactile sensors both rely on a capacitive based sensing. Exemplary detailed design and process flow of the sensors are illustrated in FIGS. 1(a)-(e) and FIGS. 2(a)-(d), and discussed in the Examples below. Further information about each sensor's principle of operation and choice of material is explained below.

In various embodiments for temperature sensors, we can use a simple resistive structure, either cut out of aluminum foil or drawn with a conductive ink, such as the silver conductive pen on the Post-it™ paper (see, e.g., FIG. 1a), The aluminum foil has an electrical resistivity of $3.83 \times 10^{-8}$ Ω.m, whereas the silver pen on paper has a resistivity in the interval of 0.05-0.2Ω/□. This slight variation in the electrical conductivity is due to the variability in filling density, The resistance of the sensor will vary with temperature due to phonon vibrations in the lattice structure of the metal, which will increase the spacing between atoms and reduce the ability of the material to properly conduct the electrical current, causing an increase in resistance. The relative resistance change vs. temperature f(T)=ΔR/R of temperature resistors (RTDs) is commonly represented by the value of the temperature coefficient of resistance (TCR). The TCR is defined as the slope of the ΔR/R=f(T) curve and can be expressed by:

$$TCR = \left(\frac{\Delta R}{\Delta T}\right) / R \tag{1}$$

Where TOR is the temperature coefficient of resistance [in °C.$^{-1}$], ΔR [in Ω] is the change in resistance corresponding to ΔT [in °C.] the change in temperature, and R [in Ω] is the initial resistance of the sensor. The theoretical TCR of silver and aluminum at 20° C. are respectively, 0.0038° C.$^{-1}$ and 0.0039° C.$^{-1}$ [51].

Figure 1B:
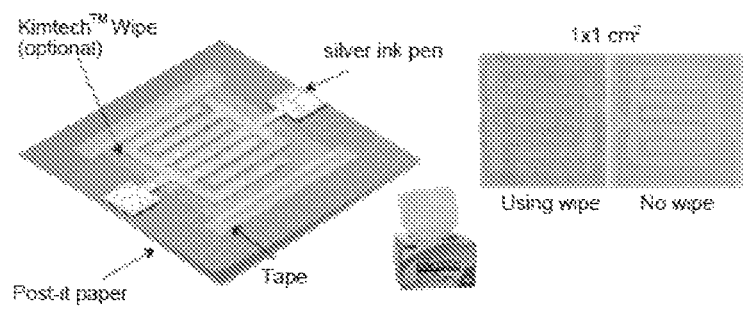

In various embodiments, for capacitive humidity sensors (See, e.g., FIG. 1(b)), paper withholds an advantageous property for measuring humidity due to its porous cellulose-fiber nature, and the adsorption and desorption of moisture on paper relative to humidity levels is a well-known phenomenon[6,52]. Paper can, thus, serve as an active material for humidity sensing. Since paper is hygroscopic, as humidity level increases, more water molecules adsorb to the hydroxyl groups on the surface of the paper, changing the relative permittivity and altering in turn the capacitance of the sensor. Water has a relative permittivity of $\epsilon_{r,water}$=80.1 at 20° C., thus the permittivity of paper is expected to increase, leading to an increase in capacitance as humidity levels rise (Equation 2):

$$C = \frac{\epsilon_0 \epsilon_r A}{d} \tag{2}$$

Where "C" is the capacitance of the sensor [in F], $\epsilon_0$ is the vacuum permittivity ($\epsilon \approx 8.854 \times 10^{-12}$ [F/m]), $\epsilon_r$ is the relative permittivity of the dielectric material in between the two conductive fingers, and "d" is the separation between the parallel conductive plates [in m]. For further electrical stability and reduction of measurement fluctuations, we have covered the sensor structure with a sheet of "KIMTECH™ wipe"[53] which shows to reduce electrical discharges, and has a relative permittivity very close to that of air, as calculated in Table 1.

Figure 1C:
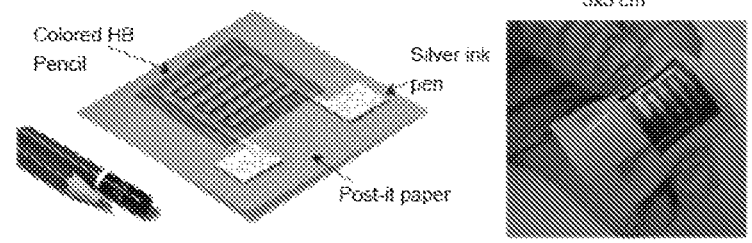

In various embodiments for pH sensors, pencil of grade HB can act as the sensing film (see, e.g., FIG. 1(c)). HB grade pencil has 68% carbon and 26% clay[54] and electrical resistivity is calculated to be $\rho$=1.85×10$^{-4}$ Ω.m. Note that ρ is highly dependent on the content of carbon, and decreases as the percentage of carbon increases. The principle of operation relies on measuring the change in resistance upon exposure to different pH levels. Since paper substrate is sensitive to moisture, once exposed to a solution (regardless of the pH level), moisture level in the paper will increase and saturate, increasing the electrical conductivity of the paper, and inducing a change in the resistance of the sensor. Nevertheless, this resistivity dependence on humidity is constant for all solutions under study, and is therefore taken as a reference. The paper effect is negligible compared to the high conductivity introduced by the pencil layer. The dominant effect is the redox reaction occurring between the graphite and hydroxyl ions in the corresponding aqueous solutions. An acidic solution has higher concentration of hydrogen ions H$^+$ than water, and a basic solution has higher concentration of hydroxide ions OH$^-$. The sensing film can exhibit changing resistivity or conductivity based on the amount of hydroxyl groups reacted. The sensing mechanism can be explained by the adsorbed ions (hydroxonium ions H$_3$O$^+$ and hydroxyl ions OH$^-$). When exposed to an alkaline solution, the carbonyl functional group goes through a reduction step (gaining electrons e), eventually transforming into methane ($CH_4$) the most highly reduced state, decreasing the resistance with respect to neutral solution resistance, Conversely, when exposed to an acidic solution, the carbon-based film goes through an oxidation step (loses $e^-$), eventually becoming $CO_2$, which is the most highly oxidized state, increasing the measured sensor's resistance.

Figure 1D:
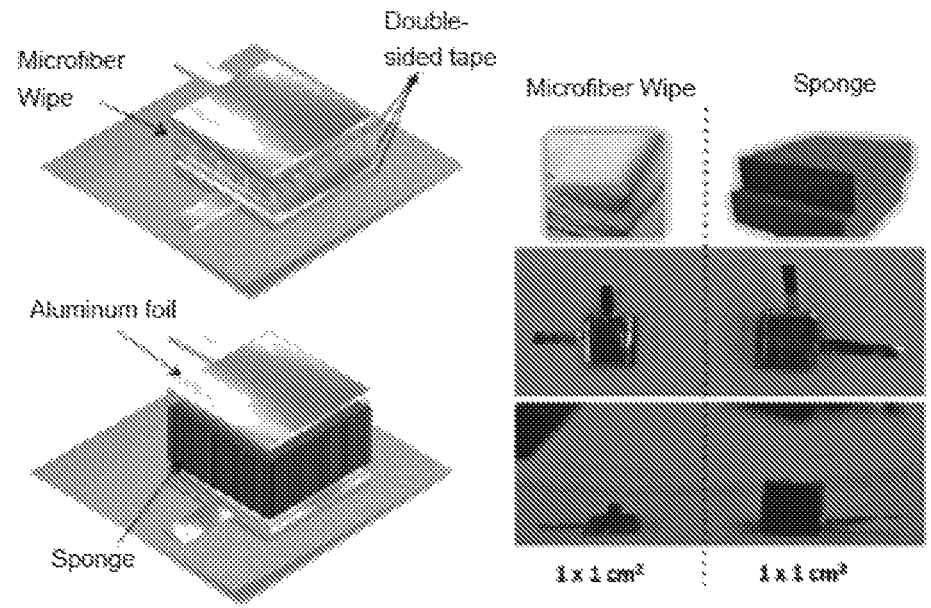
Figure 1E:
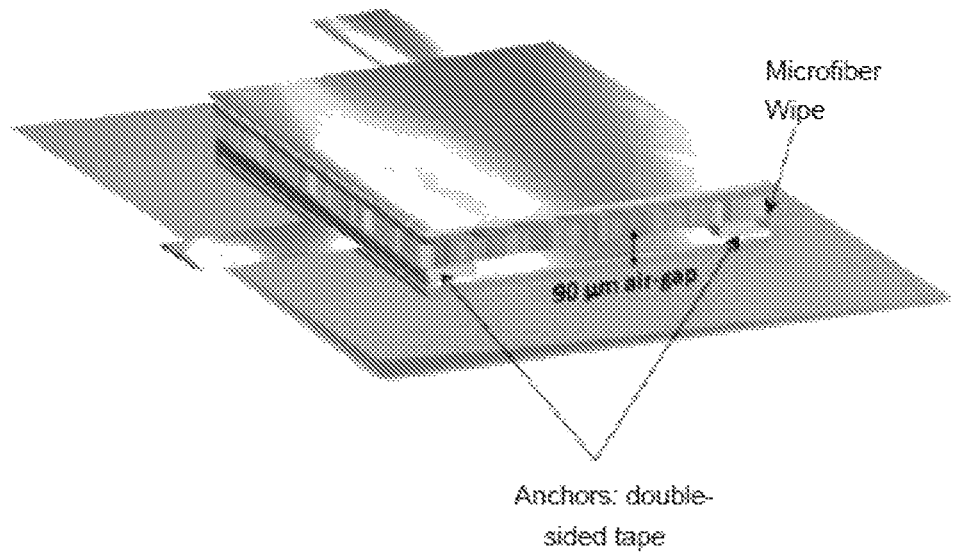

In various embodiments for pressure sensors, such as shown in FIG. 1(d), the principle of operation can be described in Equation 2. As the applied pressure increases, the dielectric thickness decreases, increasing the output capacitance of the sensor. In fact, due to the elastic deformation and porous properties, the sponge will vary in thickness as it is exposed to various external forces, Similarly, the cleanroom wipes are composed of multilayer microfiber construction; this texture allows for high sensitivity and deformation under mechanical stimuli. In order to further improve the sensor's response to lower pressure regimes, an air-gap based design was implemented, as shown in FIG. 1(e). This device geometry will allow for greater sensitivity due to the ultra-high compressibility and deformation of air. In fact, it has been shown that electrical signals from vibrations are dramatically amplified when an air gap of few micrometers in size is implemented in the sensor's structure[55].

Figures 2A, 2B, 2C, 2D:
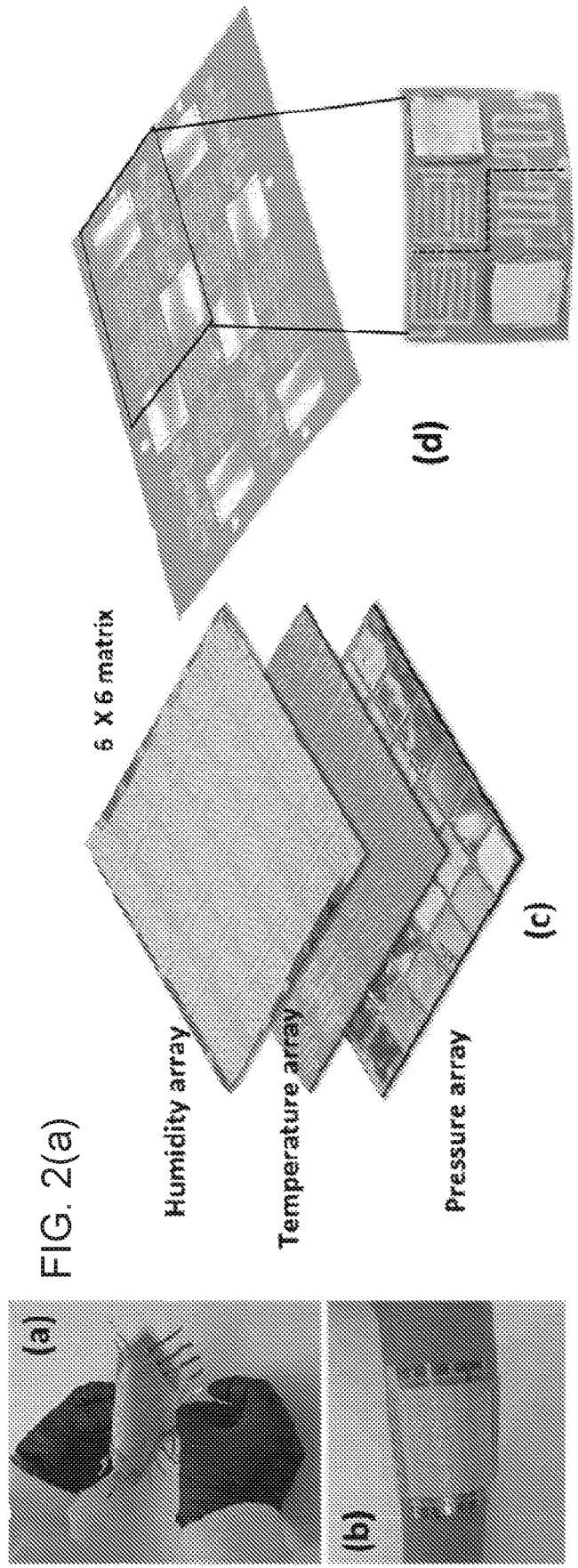

In various embodiments, we can combine two or more of the sensors into a single paper-based platform. For example, in an aspect, we built a 6×6 artificial "Paper Skin" through the superposition of multiple layers, for example three layers, of sensors networks, as shown in FIGS. 2(a)-(c). The pressure-sensing platform provides multi-functionality for force, touch, motion, direction and proximity sensing, This stacking configuration allows for simultaneous localized sensing of various external stimuli per pixel, bringing together extensive sensing functionalities in a low-cost and sustainable manner. This stacking arrangement has the advantage of having compact and localized pixels, which is beneficial for sensing surrounding behaviors. However, for human vitals detection, an in-plane integration of the sensors may be desired (FIG. 2(d)) to insure direct contact with the skin for more accurate measurements.

Material Characterization

Thickness, electrical resistivity and relative permittivity are material properties that can be given consideration in fabricating our devices and understanding their behavior. Some of these characteristics are provided in Table 1. Thickness was obtained through a high-accuracy digital micrometer; electrical resistivity using a four-point probe resistivity measurement, and relative permittivity was calculated from the measured capacitance of a 3×1 cm² capacitor, using the studied material as the dielectric. Additional material characterization was performed on the Post-it™ paper, the sponge and the microfiber cleanroom wipe, in order to examine their surface topography and verify their porosity through scanning electron microscopy (SEM).

For studying the surface topography and porosity of the different materials, we performed scanning electron microscopy (SEM). For sample preparation of the Post-it™ note, the piece of paper was blow-dried with nitrogen ($N_2$) to remove dust particles, and then coated with 2 nm layer of Iridium (Ir) to prevent charging during imaging. The SEM image in FIG. 3(a) reflects the fiber structure of the Post-it™ paper through the apparent mesh of cellulose microfibrils. Cellulose is hydrophilic and insoluble in water, which makes it perfect for our humidity sensing purposes.

As for the sponge and the microfiber cleanroom wipe, the samples were sputtered with a 2 nm layer of Ir to prevent charging, SEM images in FIGS. 3(b) and 3(c) confirm the porous nature of our chosen materials. This porosity allows more compressibility and deformation; an advantageous property for improved low-pressure sensitivity[56]. We notice that the sponge exhibits a different structure than the cleanroom wipe, where it displays a network of hallow hexagonal microstructures (pores), whereas the polypropylene wipe illustrates a network of randomly oriented microfibril threads. As shown in FIGS. 3(e) and 3(d), different areas of the wipe reveal larger separations between the microfibrils. This lower density translates into higher sensitivity to small loads. In fact, the synthetic sponge is made out of foamed polyester (PES), which is rugged, stiffer, and has higher density than the polypropylene (PP) found in the cleanroom wipes ($D_{PP}$=0.91 g/cc; $D_{PES}$=1.38 g/cc)[8]. Besides, elongation is much higher for PP, which gives better elasticity and thus more compressibility. Therefore, it is expected that the cleanroom wipe based sensor will demonstrate a higher sensitivity to pressure, whereas the sponge-based sensor will be able to have a wider range of operation in the high pressure regime, due to its larger thickness.

Figures 4A, 4B, 4C, 4D, 4E, 4F:
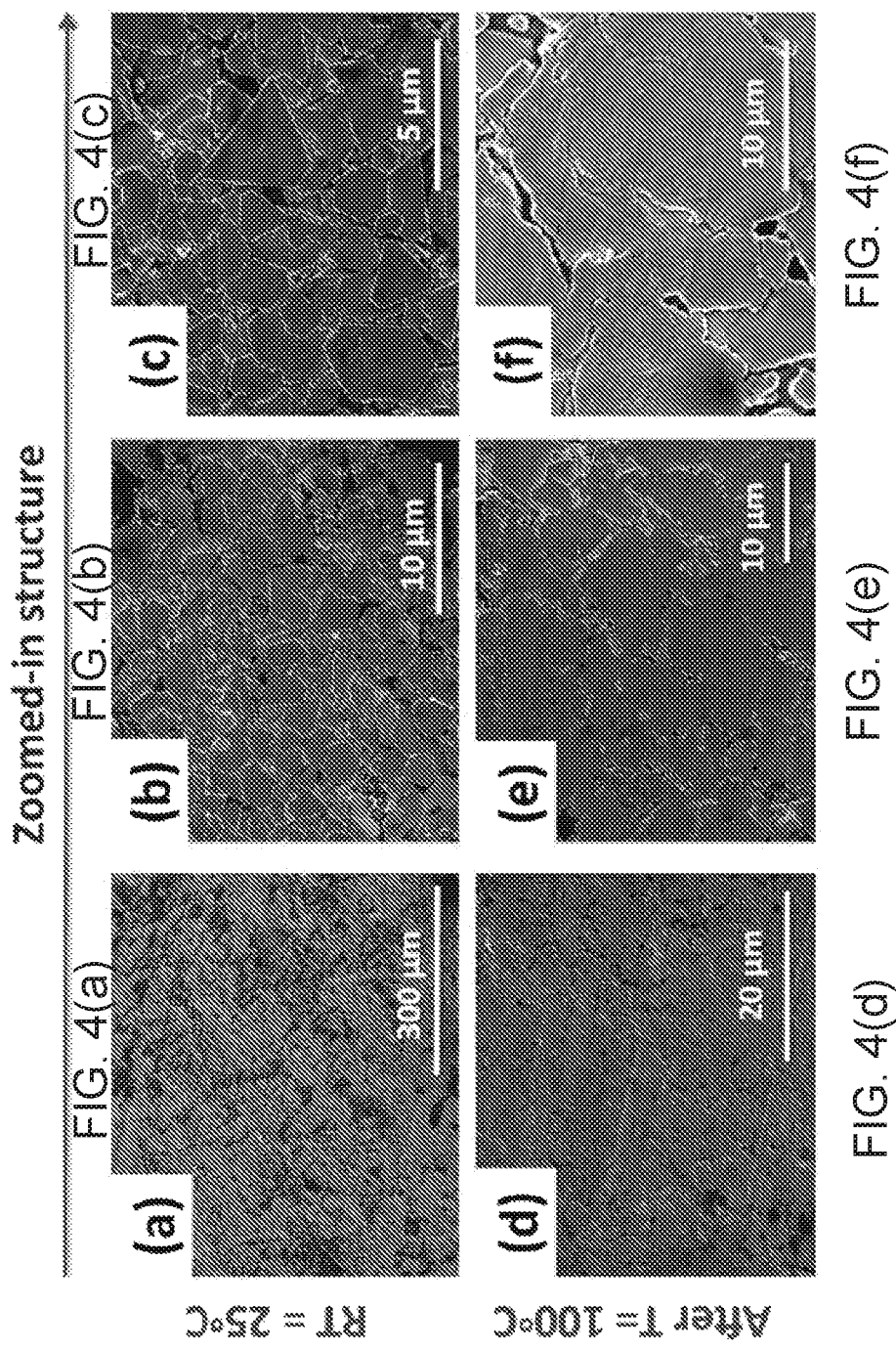

In an embodiment silver ink was used for designing temperature sensors. We studied the stability of the silver ink interconnects at high temperatures. We performed SEM on the same silver ink sheet, before and after heating the sample to 100° C. Resistance values were extracted for both cases only after the temperature of the surface came back to room temperature. FIGS. 4(a)-(c) show SEM images of the silver (Ag) ink particles before heating, where we can clearly distinguish the fairly uniform distribution of Ag hexagonal microstructures. After heating, room temperature images in FIGS. 4(d)-(f) indicate that the silver-based gel-ink pen has expanded and the enlarged Ag microstructures have superimposed. The diffusion temperature of pure Ag is determined to be above 630° C.[58], however the circuit scribe conductive pen composition is like that of any commercial gel-ink pen, except the color pigments in the pen have been replaced by silver particles. This being said, a gel medium exhibits a high liquid viscosity, described by the dynamic viscosity ($\mu$), where the viscosity of the medium tends to decrease as temperature increases, translating into a liquefied medium that promotes the superposition of Ag particles. The dynamic viscosity "$\mu$" is exponentially dependent on temperature by Reynolds' model:

$$\mu(T) = \mu_o e^{-bT} \qquad (4)$$

Where T is temperature [in ° C.], $\mu$ is the viscosity of the liquid [in Pa·s], and "$\mu0$" and "b" are empirical coefficients of the model. Moreover, at elevated temperatures the silver particles have undergone thermal expansion, in which their volume expands in response to temperature through heat transfer. The volumetric thermal expansion coefficient $\alpha_V$ of any medium is generally described by:

$$\alpha_V = \frac{1}{V}\left(\frac{\partial V}{\partial T}\right)_p \qquad (5)$$

Where 'V' is the medium's volume [$m^3$], "T" the temperature [K] and 'p' indicates that the pressure is held constant during expansion. The linear thermal expansion coefficient of silver is $\alpha_{Ag}$=18×10$^{-6}$ K$^{-1}$ [59] and since silver is an isotropic material, then the area thermal expansion coefficient becomes $2\alpha_{Ag}$ and the volumetric expansion coefficient is 3 $\alpha_{Ag}$.

Figure 5:
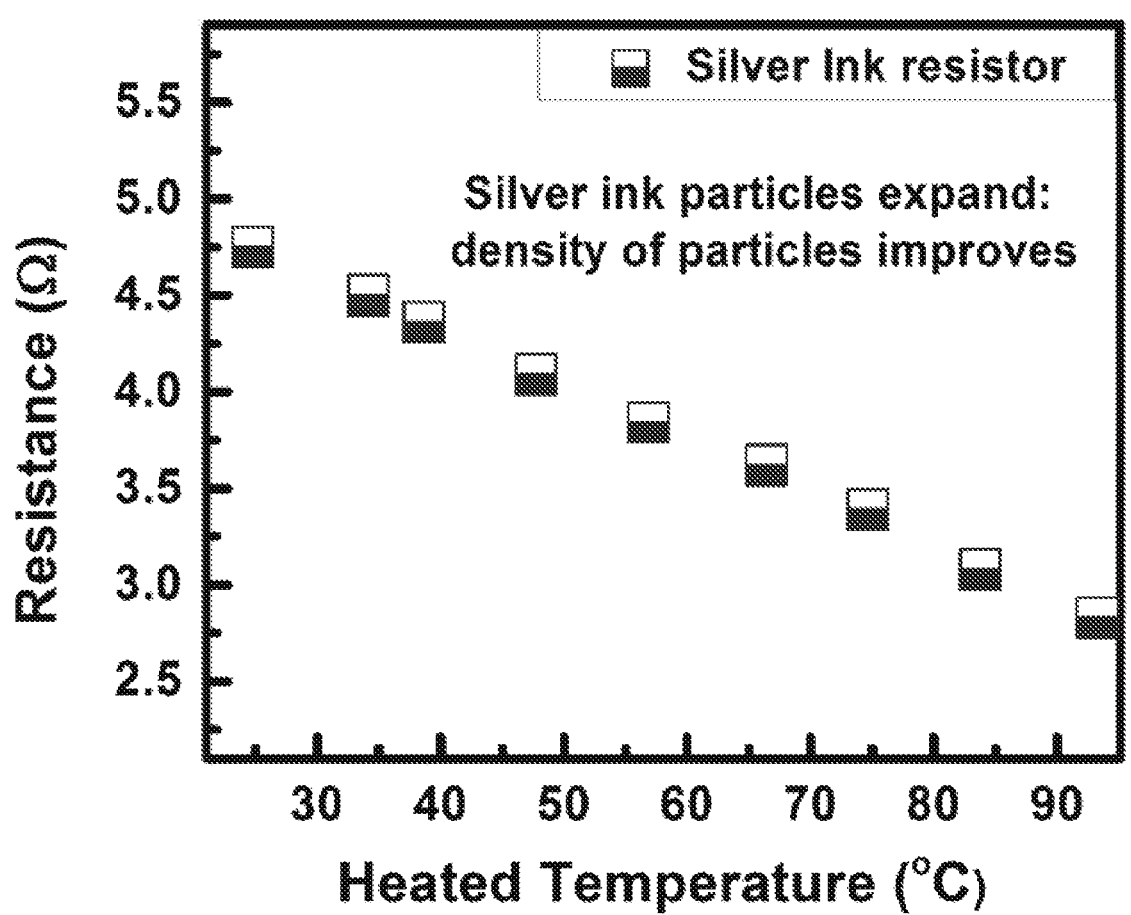
FIG. 5 depicts the resistance variation of heated silver ink film. Resistance of silver ink film on paper is shown with respect to different heating temperatures. Heated measurements are collected after the structure is cooled down to room temperature.

The results display an irreversible process where the sheet resistance of silver ink interconnects decreases due to an improvement in film density. FIG. 5 illustrates the decrease in resistance after the silver ink is heated to temperatures up to 100° C. Resistance decreases from 4.75Ω at room temperature (25° C.) down to 2.83Ω after heating to ~95° C. Note that for each measurement, the resistance value was taken after the conductive ink cooled down to room temperature, and not while heated.

Electrical Characterization and Analysis

Provided below is an electrical characterization and analysis of various sensors that can be made using our paper-based electronics platform. Each sensor characterization begins with the study of the behavior and sensitivity of the sensor, and then we record the response and performance of the sensors in a temporal study where the sensors undergo different external stimuli.

Temperature Sensing

Figures 6A, 6B:
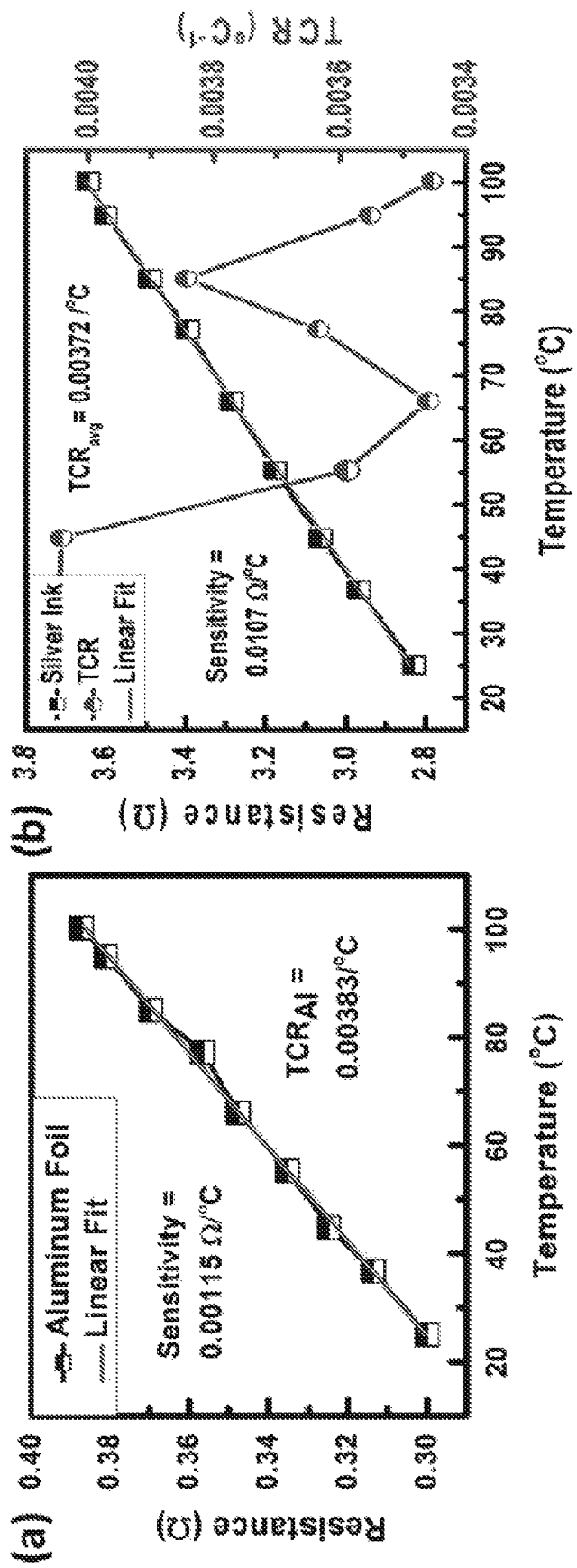
FIGS. 6(a) and (b) depict a comparative study of silver ink versus aluminum foil based temperature sensors.
FIG. 6(b) is a plot of a silver ink based temperature sensor, illustrating a sensitivity of 0.0107Ω/° C.

We evaluated the temperature sensor behavior, comparing a silver ink based sensor with an aluminum foil based sensor. To compare the silver ink based sensor with the one made out of aluminum foil, the silver ink based sensor was used after it was heated to 100° C. and cooled down. Then, we characterized each sensor on a thermal chuck manual probe station, where the chuck is heated from 25° C. up to 100° C. with steps of 10° C. For precision, the temperature on the surface of the sensor was measured using a thermocouple and the resistance value collected using a digital multimeter. FIGS. 6(a) and (b) that both sensors exhibit a linear behavior where resistance increases with respect to temperature. The calculated temperature coefficient of resistance (TCR) for aluminum foil and silver ink pen are respectively $TCR_{exp, Al}$=0.00383/° C. and $TCR_{exp, Ag}$=0.00372/° C. Our experimental values very closely match the materials' theoretical TCR values of $TCR_{th, Al}$=0.0039/° C. with a relative % error of 1.8% and $TCR_{th, Ag}$=0.0038/° C. with a relative % error of 2.1%[51].

Figure 7A:
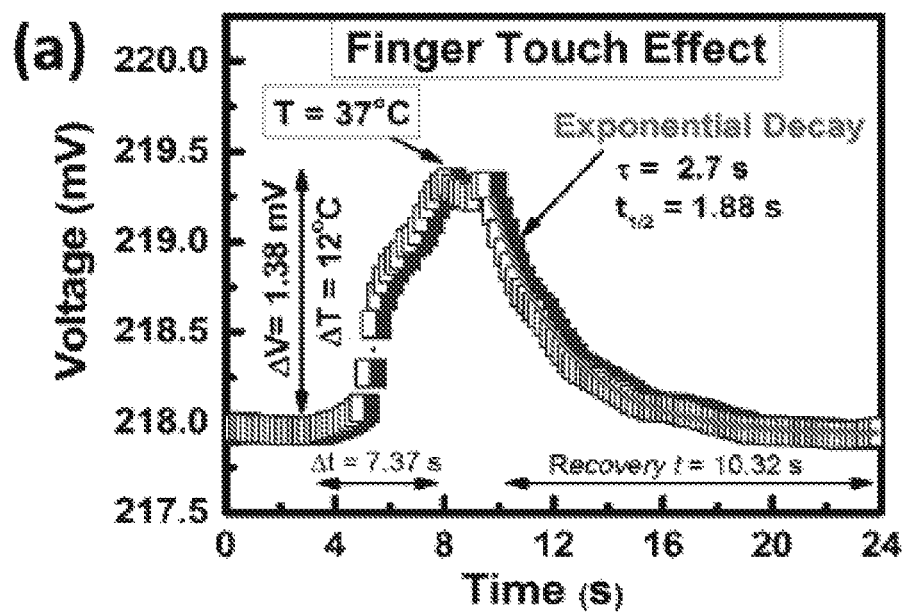
Figure 7B:
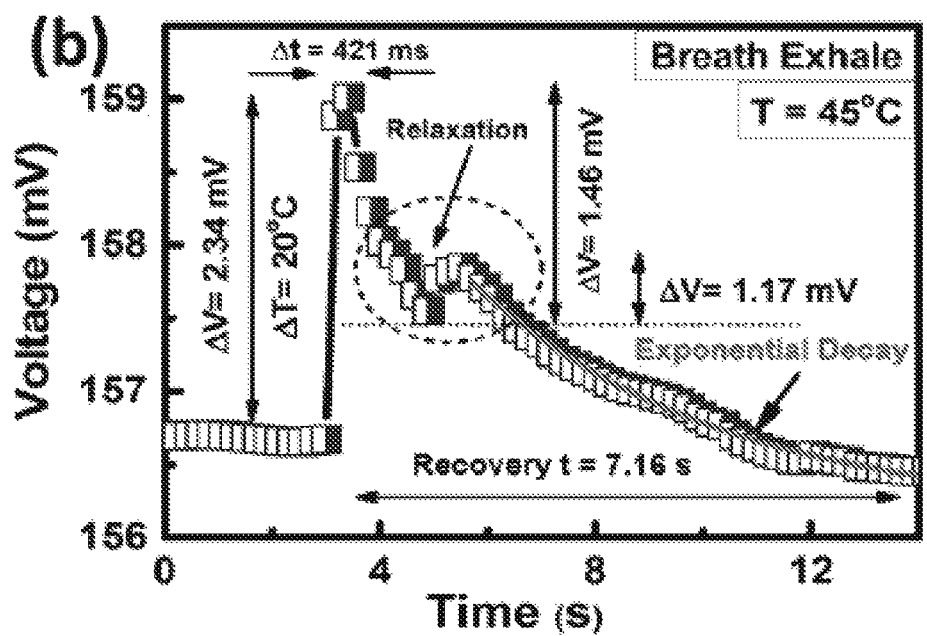
Figure 7C:
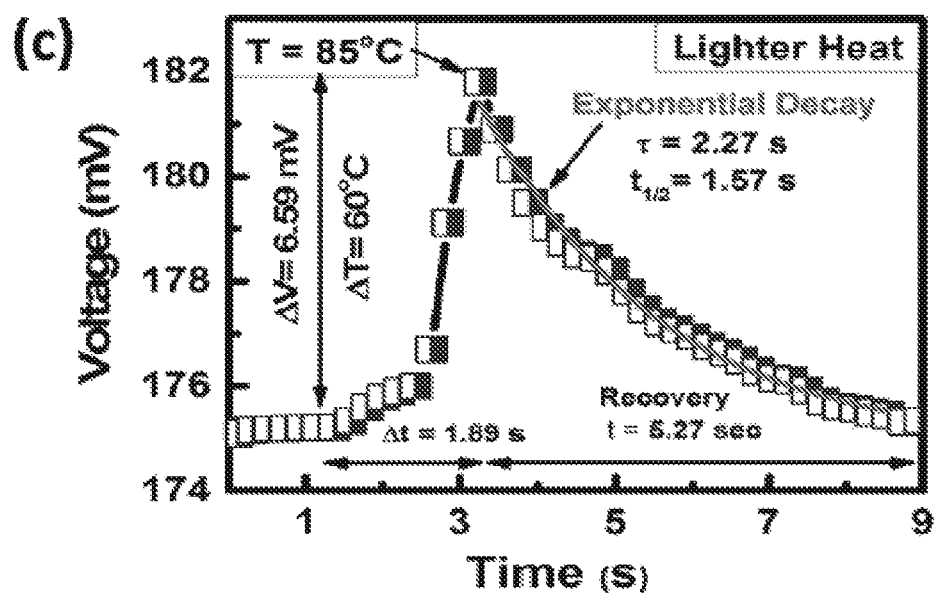

As for real-time sensing, FIG. 7(a) shows the Gaussian/Lorentzian profile of the sensor's response to human touch. The maximum change in voltage is ΔV=1.38 mV corresponding to a change in temperature of ΔT=12° C. relative to room temperature. The total response time of the sensor is 7.37 seconds and the total time for the sensor to recover its initial state is 10.32 seconds The recovery takes the shape of an exponential decay from which we can retrieve the rate of decay by extracting the mean lifetime T or half-life $t_{1/2}$ of the sensor, corresponding to the time required for the sensor to fall back to half of its initial value. In this case, the half-life of the sensor was determined to be $t_{1/2}$=1.88 seconds. For breath temperature detection (FIG. 7(b)), the maximum change in voltage is ΔV=2.34 mV corresponding to a change in temperature of ΔT=20° C. relative to room temperature. The sensor exhibits a spike response time of 421 ms, with a total recovery time of 7.16 seconds. For the final test, we position the flame of a lighter about 10 cm away from the surface of the sensor. FIG. 7(c) shows the originated change in voltage in response to the flame's heat. The peak change recorded is ΔV=6.59 mV corresponding to ΔT=60° C. The total response time is about 1.89 seconds, with the fastest total recovery time of 5.27 seconds.

The results demonstrate that the silver ink based sensor can be 9 times more sensitive than the aluminum foil based temperature sensor, with respective sensitivities SAg=0.0107Ω/° C. and SAl=0.00115Ω/° C., as shown in FIGS. 6(a) and (b).

For arraying purposes, we continued our studies with the silver ink based sensor. We performed temporal study measurements, where we exposed the sensor to very common external stimuli that we encounter in everyday life. We tested the temperature sensor's real-time response to human touch (T=37° C.) (FIG. 8(a)), human exhaled breath (around 42° C.) (FIG. 8(c)), and from a lighter flame positioned 10 cm away from the sensor (T~85° C.) (FIG. 8(e)). Comprehensive results are shown in FIGS. 8(a)-(i) and FIGS. 7(a)-(c).

Figure 8A:
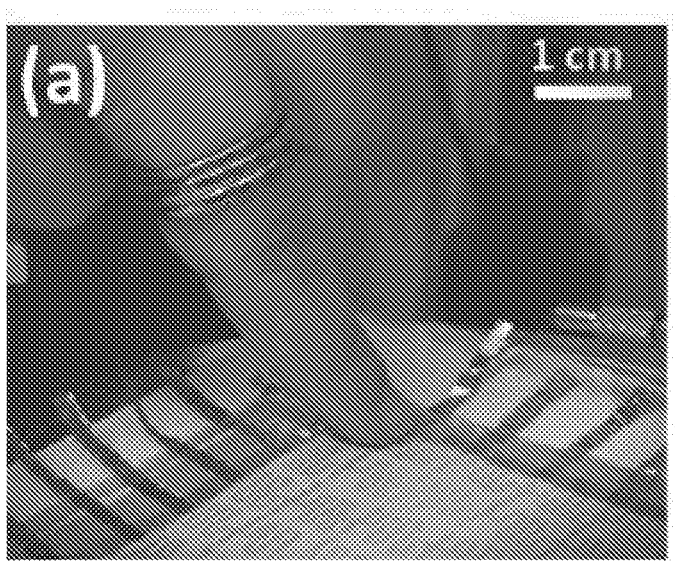
Figure 8C:
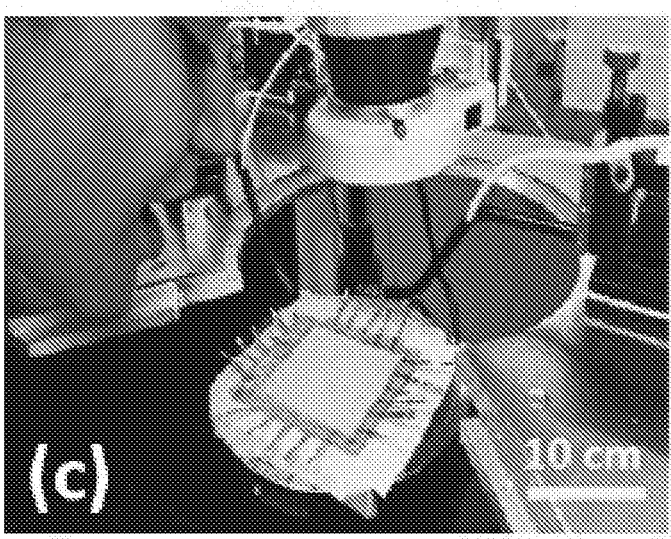
Figure 8E:
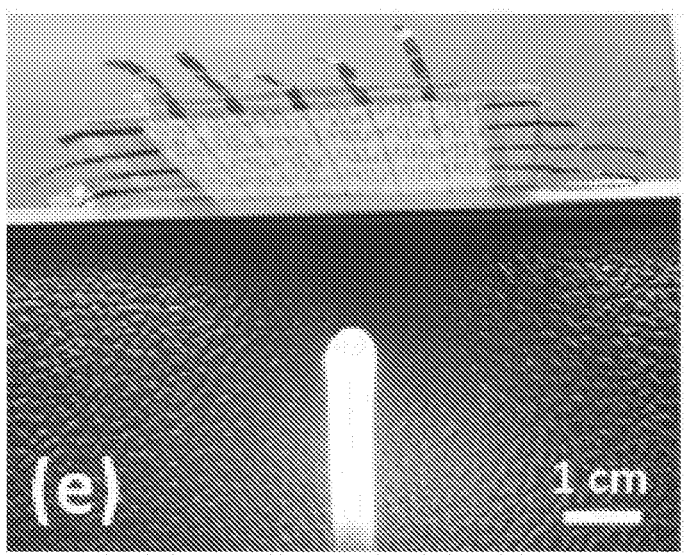
Figure 8B:
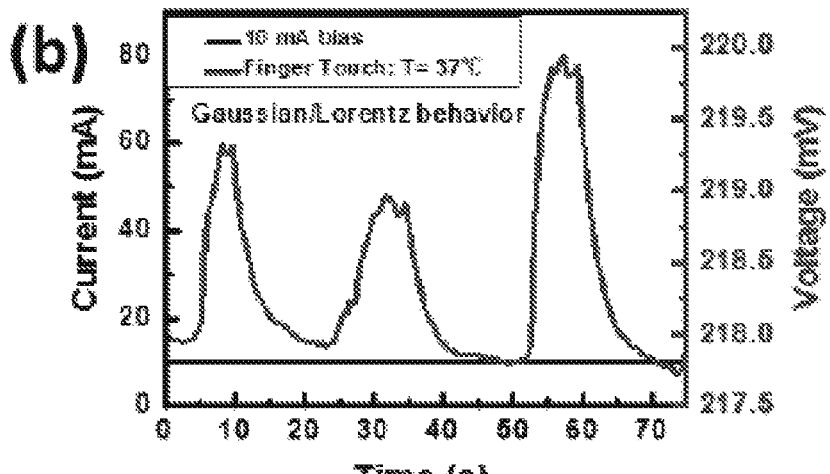
Figure 8D:
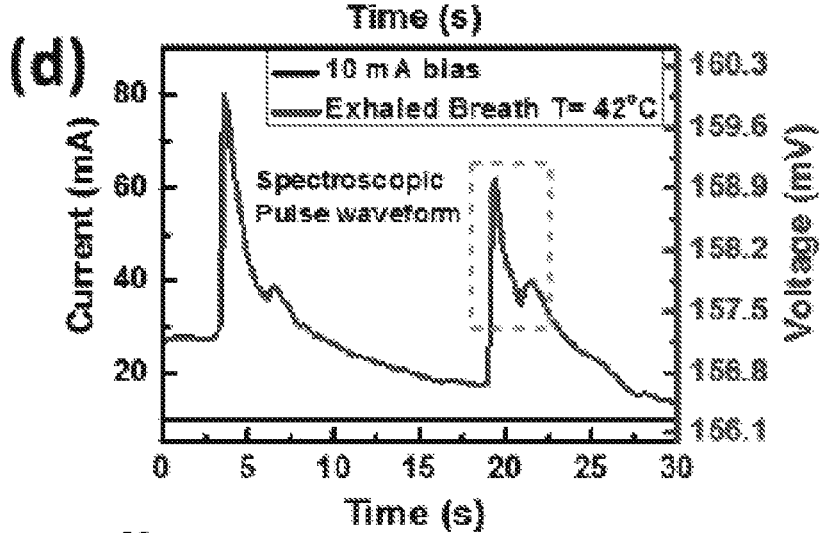
Figure 8F:
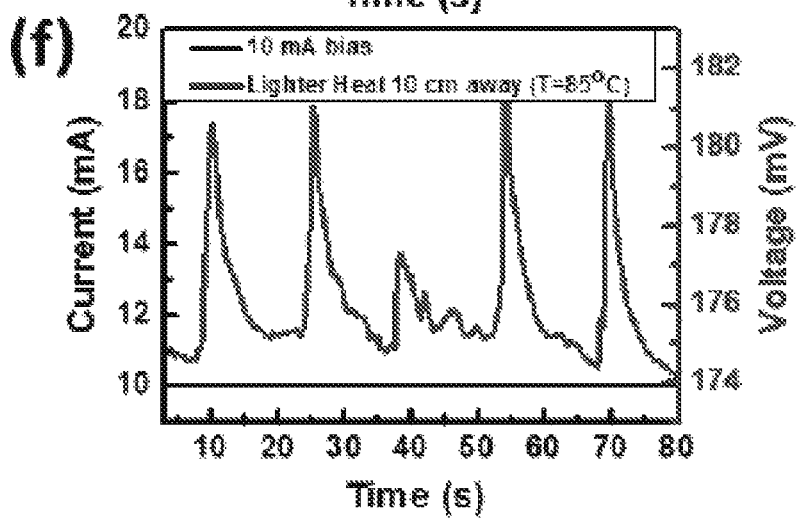
Figure 8G:
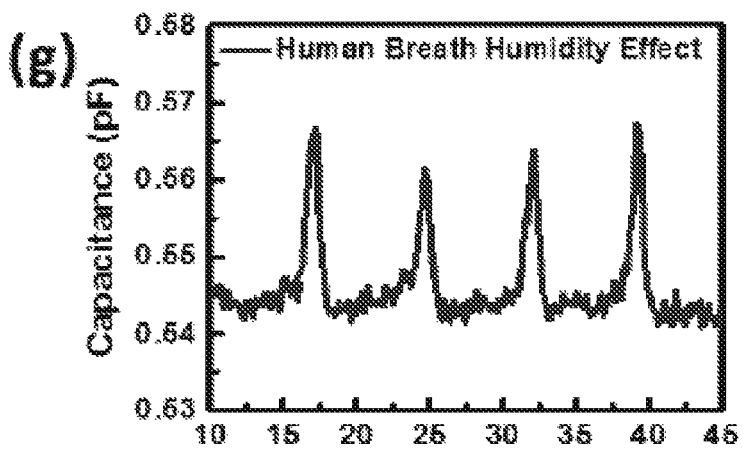
Figure 8H:
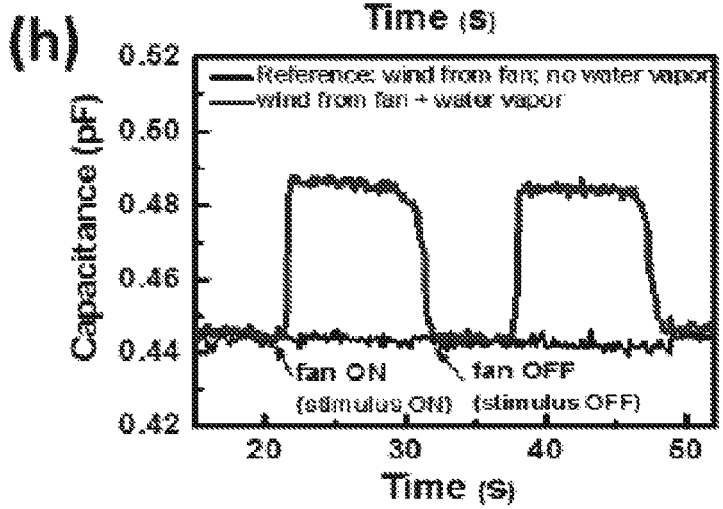
Figure 8I:

Our paper-based temperature sensors show high sensitivity to the point of detecting the spectroscopic behavior of the exhaled breath (FIG. 8d). This signal originates from the pulsating nature of our breathing process, controlled by our heart rate[33]. We report ultra—fast response and recovery times of 421 ms and 5.27 s respectively, compared to 20 s response and 30 s recovery time reported in the previously published literature[34].

Humidity Sensing

We studied the behavior of the humidity sensor by exposing it to three different values of known humidity levels: room temperature (46%), human breath (76%), and water vapor (97%). FIG. 9(d) is a photograph of the experimental setup for applying water vapor on the surface of the humidity sensor. These humidity values were determined using a commercial humidity sensor. As expected, FIG. 9(a) shows a nearly linear increase in the capacitance as humidity level increases. The maximum calculated sensitivity is 0.18%/% RH, which is quite low compared to values reported in the literature[35,36], but still we show a very repeatable behavior with fast adsorption and desorption times. Temporal study was conducted for the different external stimuli. See, e.g. FIGS. 8(g)-(i).

Figure 9B:
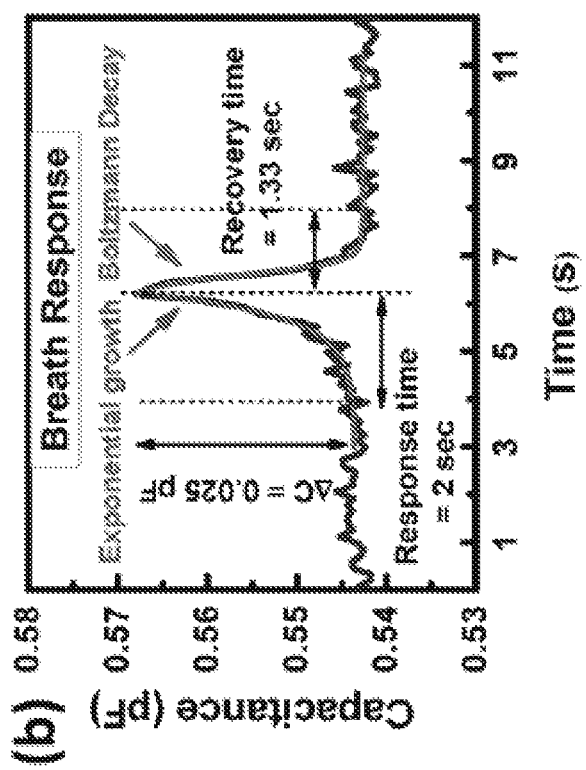
Figure 9A:
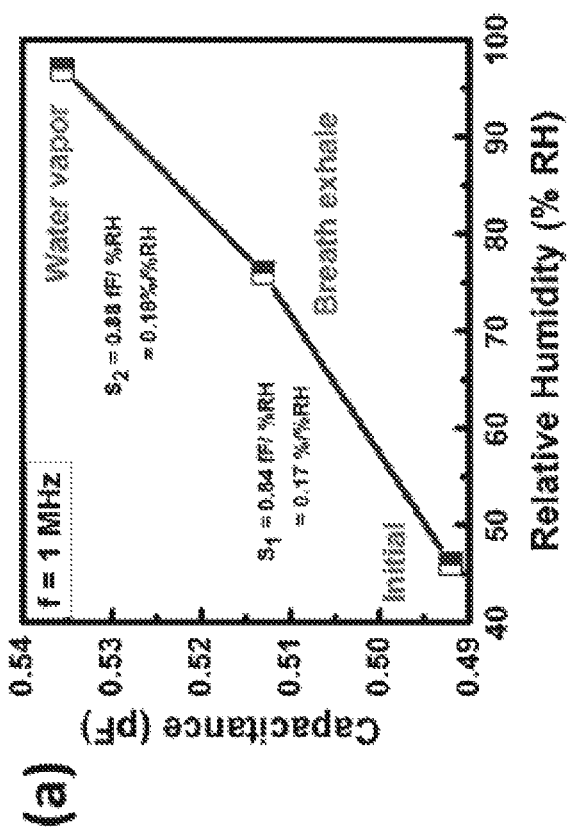
Figure 9D:
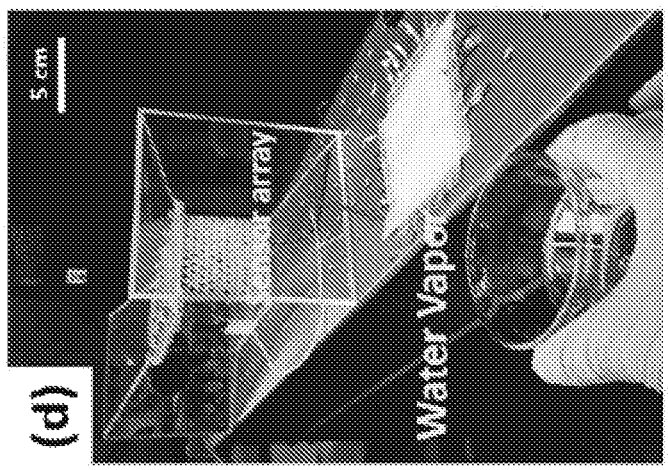
Figure 9C:
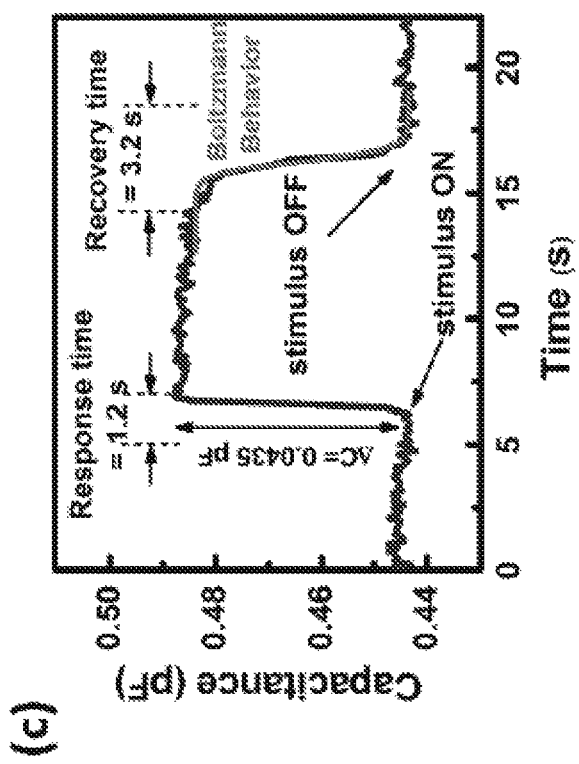

For real-time breath humidity experiment, FIG. 9(b) shows an increase of 0.025 pF in capacitance as a response to 76% relative humidity. We show a very fast total response time of 2 seconds, with an exceptional growth behavior with half-life time $T_{1/2}$=0.34 seconds. As for the recovery of the sensor, the desorption follows a Boltzmann profile, with total recovery time of 1.33 seconds, For the water vapor experiment, the time study in FIG. 9(c) demonstrates that the activation of the wind tunnel fan has no effect on the response of our sensor, guaranteeing that the behavior seen is solely from the vapor humidity. In this case, the sensor has a total response time of 1.2 seconds and a recovery time of 3.2 seconds.

On average, although the sensitivity reported is not so high, however we report very fast response and recovery times of ~1 s and 1.33 s respectively, nearly 10 times faster than the ones found in the literature using complex fabrication processes and expensivematerials[37-39].

pH Sensing

Figure 10A:
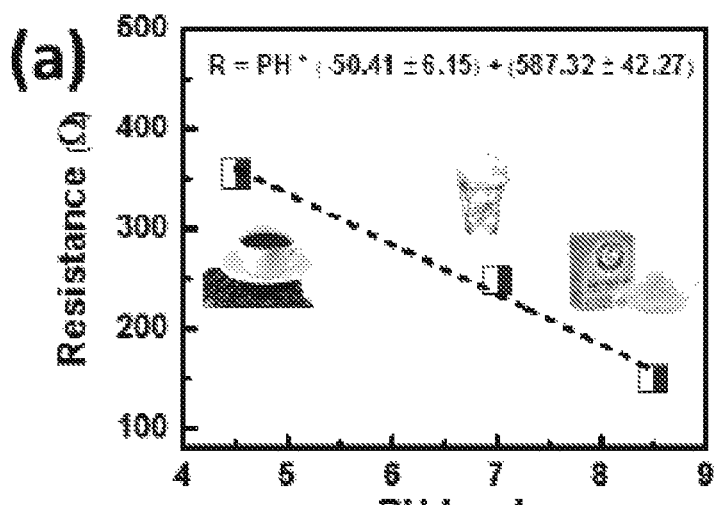

For pH sensor evaluation, we used three different solutions with distinct pH levels as follows: water (pH=7), diluted baking soda solution (pH=8.5), and Nescafé™ coffee (pH=4.5), where pH values were collected using pH test strips. Plotting the current vs. voltage plot for every solution, we retrieved the associated resistance value. We first measured the reference resistance of the sensor then we drop 2 mL of studied solution on the pH sensing film. During experimentation, we noticed that the paper was absorbing fluid after some time and was not surviving two consecutive measurements. Thus, we decided to report it as a disposable sensor, valid for one-time use. Therefore, we drew three similar pH sensors and used each one of them for one testing solution. The initial reference resistance was recorded for each sensor ($R_i$), then the final resistance ($R_f$) was measured after solution exposure, and we evaluate the change in resistance $\Delta R_{pH}=|R_f-R_i|$ corresponding to a change in pH level. FIG. 10(a) shows the plot of resistance versus pH level. The resistance shown is the average resistance calculated from the addition $\Delta R_{pH}$ to a common reference resistance $R_{ref}$.

The decrease in resistance as pH level increases (FIG. 10(a)) is in accordance with the behavior reported in the literature for graphite-based pH sensors[40-42]. The resistance respectively increases to 355Ω at pH=4.5 and decreases to 150Ω at pH=8.5, with respect to the reference resistance value at pH=7, shown in FIG. 10(a). The reported pH sensor is disposable and valid for one-time use; useful for detecting whether a solution is an acid or a base, associated to either an increase or decrease in the reference resistance of a neutral solution, Pressure/Force Sensing We also compared the pressure sensing behavior of a sponge-based sensor versus a cleanroom wipe based sensor (FIG. 10(d)). The comparative results between sponge and cleanroom wipe based sensor are shown in FIG. 10(b). We observe two linear regimes where the pressure sensitivities in the low-pressure interval [0-190 Pa] are $S_{1,sponge}$=0.09 pF/kPa and $S_{1,wipe}$=0.5 pF/kPa respectively for the sponge and wipebased sensor. As for the high-pressure regime above 200 Pa, $S_{2,sponge}$=0.045 pF/kPa and $S_{2,wipe}$=0.15 pF/kPa. As predicted by our material analysis, the cleanroom wipe exhibits higher-pressure sensitivity due to its microfibril structure that is more sensitive to smaller deformations. Then, we tested both sensors for maximum load detection, and we observed that the sponge-based sensor had a larger window for high-pressure detections, with sensing capabilities up to 90 kPa before saturation. Whereas the cleanroom wipe-based sensor entered the saturation mode after 9 kPa of applied pressure.

Results in FIG. 10(b) show that the sponge offers 10 times wider high-pressure detection window, whereas the cleanroom wipe offers 6 to 8 times higher sensitivities in the lower pressure regimes due to its highly deformable microfibril structure.

We characterized the second pressure structure fabricated for the paper skin (FIG. 1(e)). First, we studied the sensitivity of the sensor by applying small weight loads of PDMS (FIG. 10(c)), and then we performed real-time analysis in response to different external stimuli such as: high pressure exerted with the bottom of a pen (12 kPa) (FIG. 10(e)), touch/tactile detection (3 kPa) (FIG. 10(g)), and low-pressure detections from air flow exposure (down to 9 Pa) (see, FIGS. 11(a)-(c)).

Figure 10D:
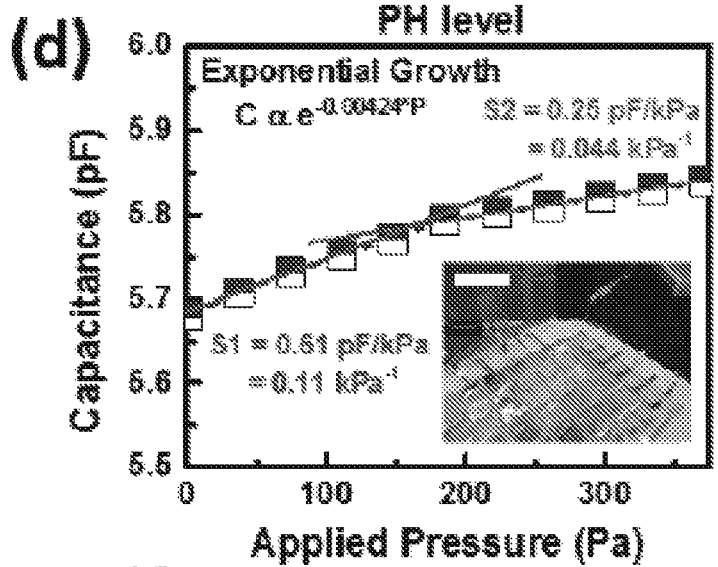

We characterized the second air-gap structure of pressure sensor, FIG. 10(d) shows an exponential growth in response to pressure. The plot can be divided into two linear regimes where the pressure sensitivity is $S_1$=0.61 pF/kPa in the low-pressure interval [0-190 Pa], and $S_2$=0.25 pF/kPa in the high-pressure regime above 200 Pa. To exert higher pressures, we study in FIG. 10(e) the real-time response of the sensor due an applied force of 12 kPa, exerted with the bottom of a pen. The pressure response time is measured to be 130 ms and the total recovery time is 13.67 seconds with an ultra-fast half-life time measured to be $t_{1/2}$=360 ms (FIG. 10(f)), We recorded very fast response and recovery times, with pressure sensitivities of 0.11 $kPa^{-1}$ and 0.044 $kPa^{-1}$ (FIG. 10(d)), comparable or even greater values compared to reported flexible capacitive pressure sensors: 0.23 $kPa^{-[43]}$, 0.0004 $kPa^{-1}$ [44], 0.0002 $kPa^{-1}$ [45]. Our response time could have been measured to be faster, but was limited to 130 ms due to our sampling rate limitations.

Figure 10G:
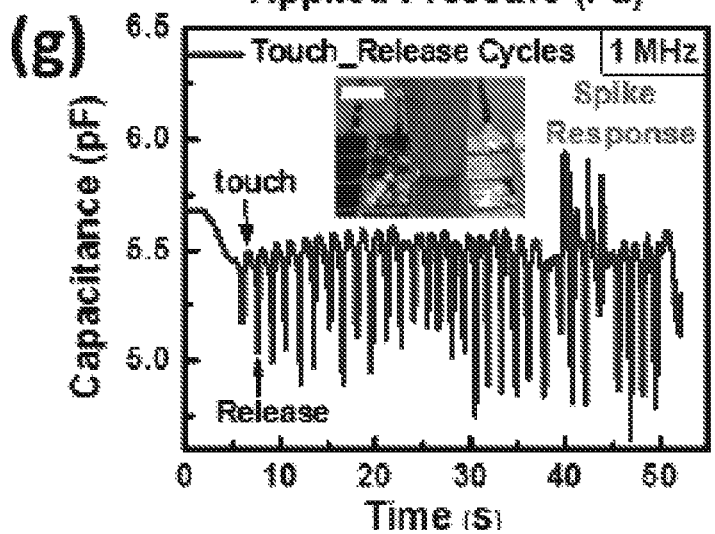
Figure 10B:
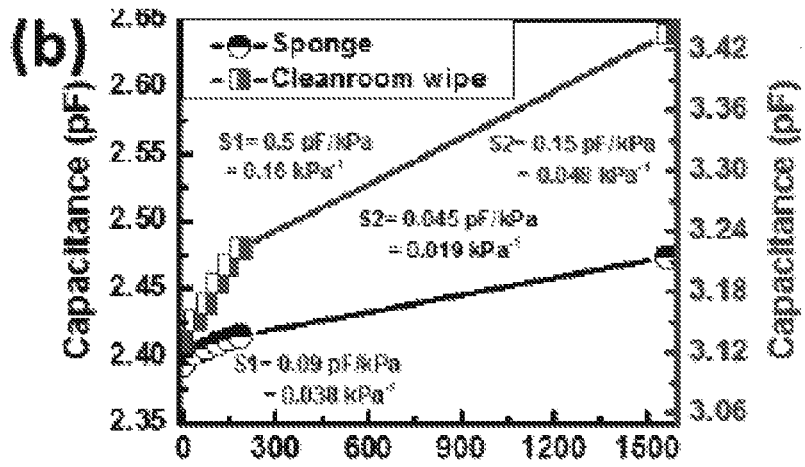
Figure 10E:
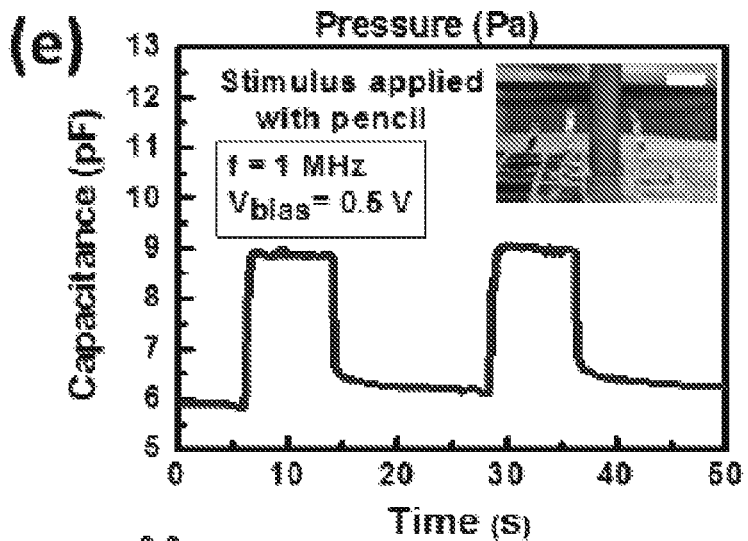
Figure 10H:
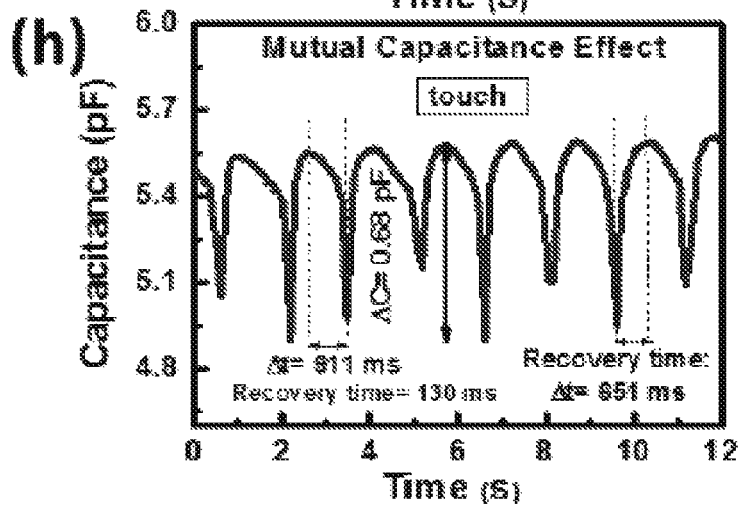
Figure 10C:
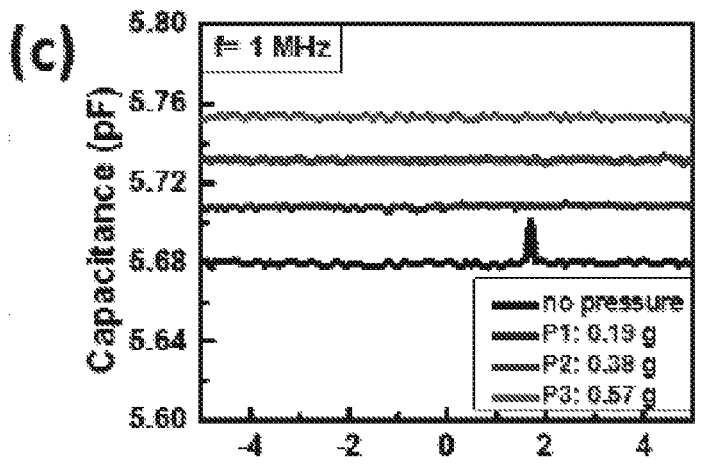
Figure 10F:
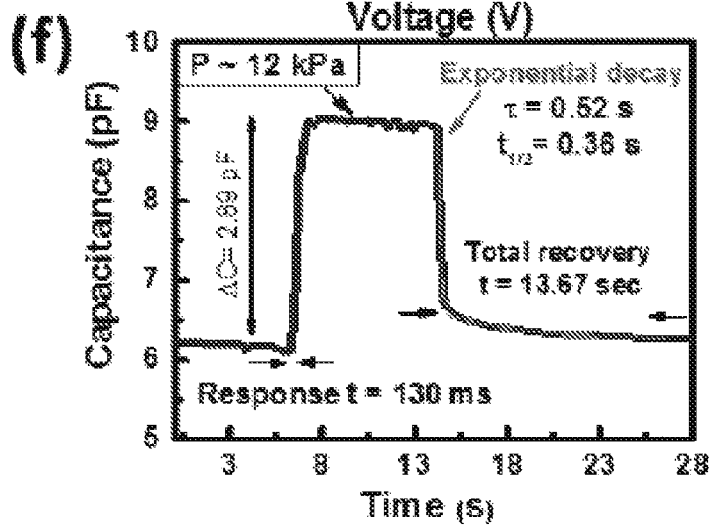
Figure 10I:
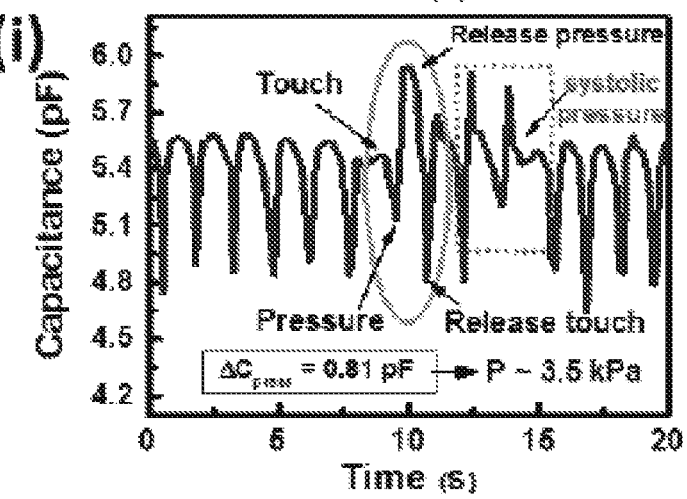

Furthermore, we studied the effect of a light human touch, which is about a couple of kPa, FIG. 10(g) shows repetitive cycles of touch and release, where the capacitance exponentially decreases once the sensor is touched. This capacitive touch effect is described by the mutual capacitance phenomenon where our finger interferes with the electric field around the capacitor (cross-talk caused by finger) and transfers part of the charge into our conductive and grounded body, hence decreasing the charge collected by the capacitor. FIG. 10(h) illustrates a sharp response to touch, with a total response time $\Delta T$=911 ms and a total recovery time of 651 ms. And when further pressure is applied with finger (~3.5 kPa), the capacitance goes up again as depicted in FIG. 10(i), following a pulsating behavior. The waveform seen reflects the pulsating breathing effect, and highlights the efficiency of our device in applications for blood pressure monitoring through the arterial pulses on our wrist.

Sharp tactile detection was possible through the mutual capacitance phenomenon and characterized by a decrease in capacitance in response to touch, as seen in FIGS. 10(g)-(h). Systolic pressure was detected in FIG. 10(i) through touch pressure, highlighting the efficiency of our device in applications for blood pressure monitoring.

Figure 11A:
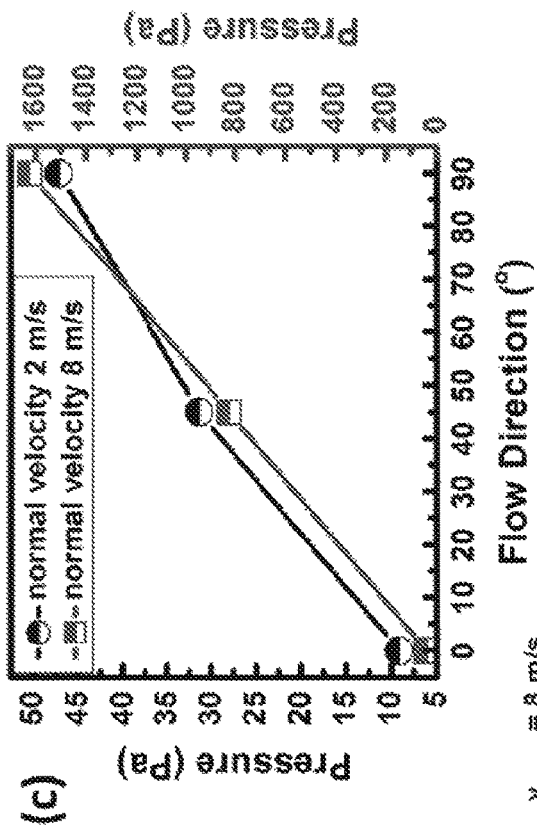
Figure 11C:
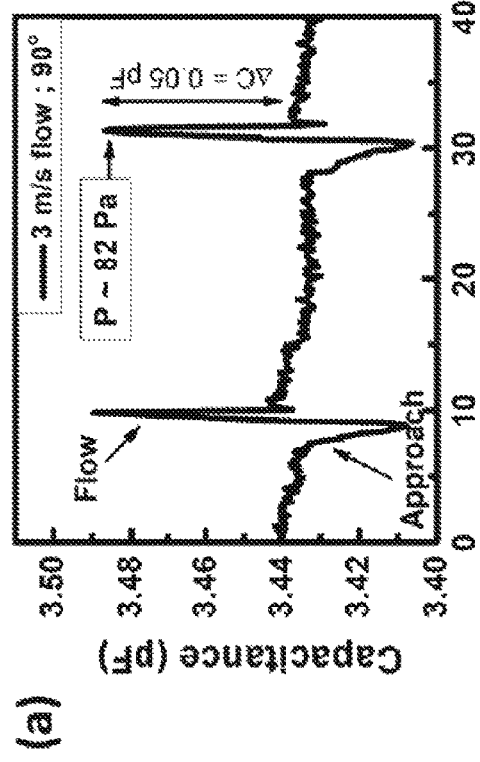
Figure 11B:
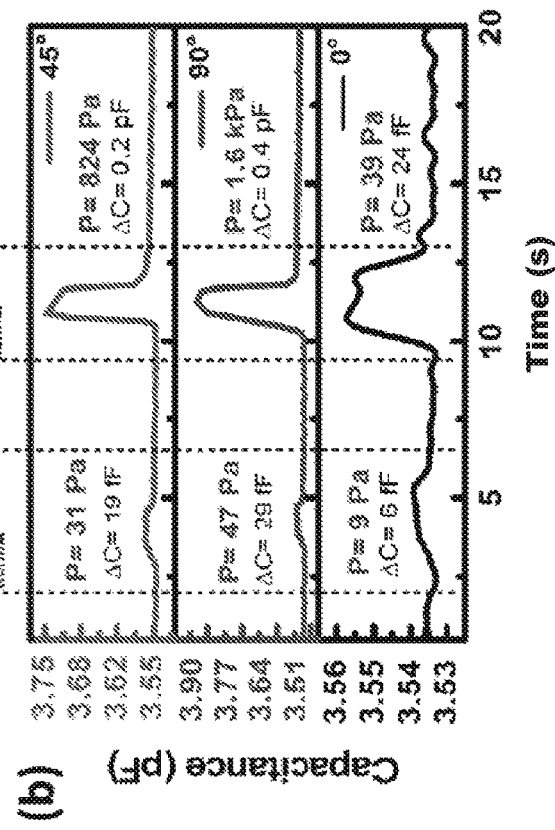

To evaluate the sensor efficiency in detecting lower pressure regimes, we applied air pressures with different flow velocities. FIG. 11(a) shows the pressure behavior to airflow at $v_{normal}$=3 m/s. The total response time is as fast as 1.04 seconds, and the total recovery time is only 2.34 seconds. Based on the detected change in capacitance, our pressure sensor successfully detected an exerted pressure of 82 Pa. FIG. 11(b) shows the pressure response to different flow orientations (0°, 45° and 90°), for two velocity values: 2 m/s and 8 m/s, The sensor successfully detected a pressure change even when the air was blown in a tangential manner (0° orientation), with a calculated pressure as low as 9 Pa for a velocity flow of 2 mis. As expected, the detected pressure increases as the vector orientation comes closer to the normal direction (FIG. 11(c)), where all the force vectors become concentrated towards the normal surface of the sensor. Note that our pressure response time was limited to 130 ms due to our sampling rate limitation in our measurement tool. In reality, the response time could be measured to be much faster. FIGS. 11(a)-(c) show the ability to detect air pressures as low as 9 Pa, with sensitivity to different speeds and flow orientations.

Figures 12A, 12B:
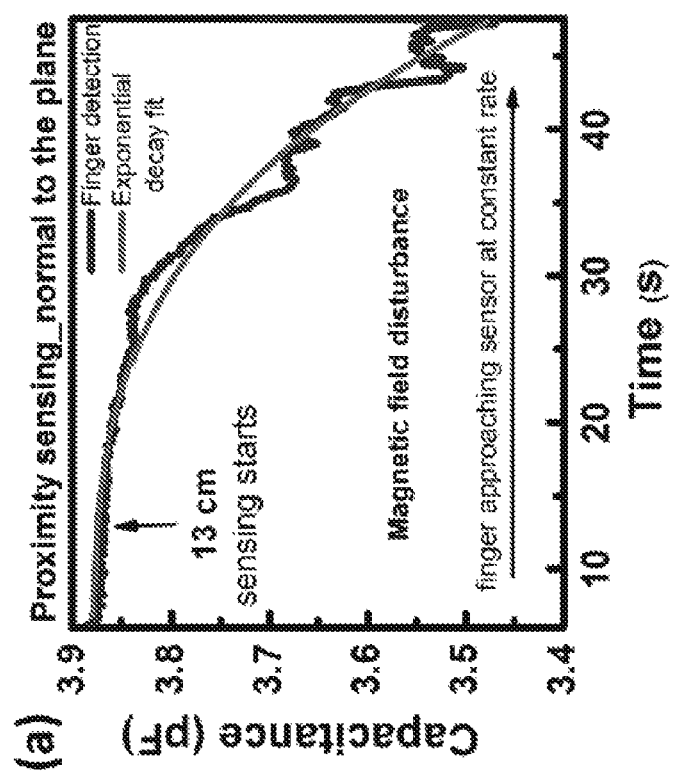

We also demonstrated the proximity sensing capabilities of our capacitive pressure sensor. The magnetic field generated around the capacitor is further enhanced due to the paramagnetic properties of aluminum foil, allowing a great extension of the field. Thus, as the human finger or body gets closer to the capacitor, the magnetic field is disturbed from a far range and the total charge gets redirected from the capacitor towards the detected conductor (in this case our body), correspondingly decreasing the measured device capacitance. FIG. 12(a) shows that as we approach the sensor at a constant rate, the capacitance respectively decreases in an exponential fashion. C-V data was then collected separately for specific distances away from the sensors. FIG. 12(b) illustrates the exponential decrease in capacitance with decreased detection range, with maximum change in capacitance $\Delta C$=0.55 pF corresponding to a detection range down to 0.5 cm. Our pressure-sensing device demonstrated outstanding proximity sensing capabilities, with 13 cm detection limit as shown in FIGS. 12(a) and (b).

Our paper based pressure sensor exhibits exceptional multi-functionality, with notable sensing potentials for pressure, touch, proximity, and directionality. The distinct responses received for pressure and touch/proximity allow for improved differentiation between multiple mechanical stimuli, enhancing user recognition for touchless control panel applications.

Paper Skin Spatial and Temporal Mapping

One major attribute of human skin is simultaneous sensing. To mimic such behavior and for proof-of-concept in large-scale monitoring applications, we demonstrate the spatial real-time mapping of the fabricated 3D stacked paper skin. We simultaneously resolved spatial and temporal information from external stimuli such as touch, pressure and humid breath, in order to test the skin-like sensing capabilities. Pressure, temperature and humidity mapping have all shown robust and concise simultaneous and localized responses (FIGS. 13(a)-(h)).

Figures 13A, 13C, 13E:
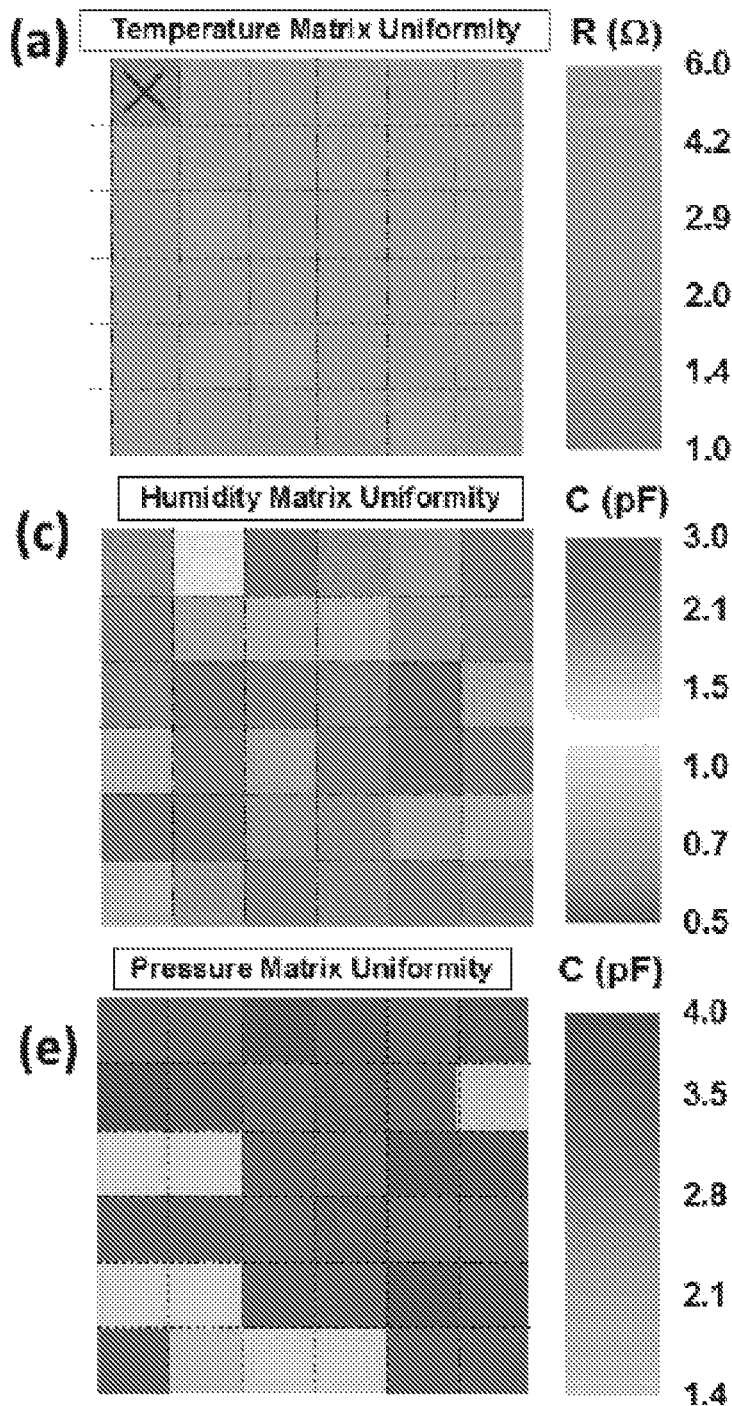
Figure 13B:
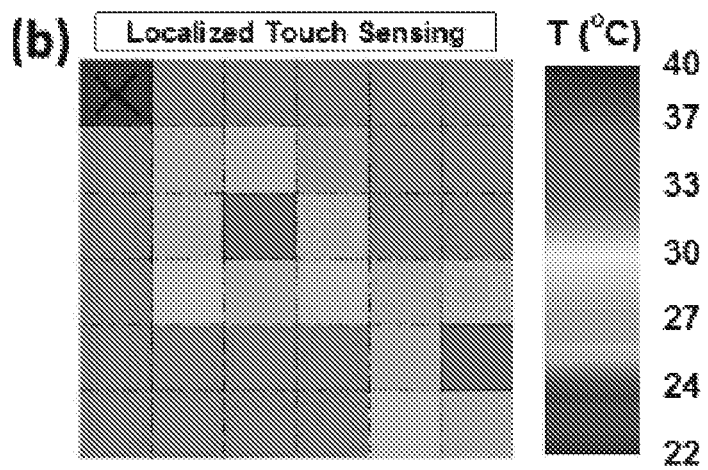

To conduct real-time simultaneous sensing on the paper skin, we first started by applying localized human touch, on pixels R3-C3 and R5-C6 and monitored the response from body heat generation. Mapping was done by applying a bias current of 10 mA, and temperature was calculated from the measured resistance change per pixel. FIG. 13(b) shows the capability of our paper-based electronic skin to detect the temperature distribution on the pixels generated from the localized finger touch. Real-time temperature monitoring identifies a generated heat of around 34° C. on pixels R3-C3 and R5-C6, which is very close to the temperature of the human body, Some of the surrounding pixels have exhibited a slight increase in temperature (at most +1° C.), which is expected due to heat radiation from the finger.

Figure 13D:
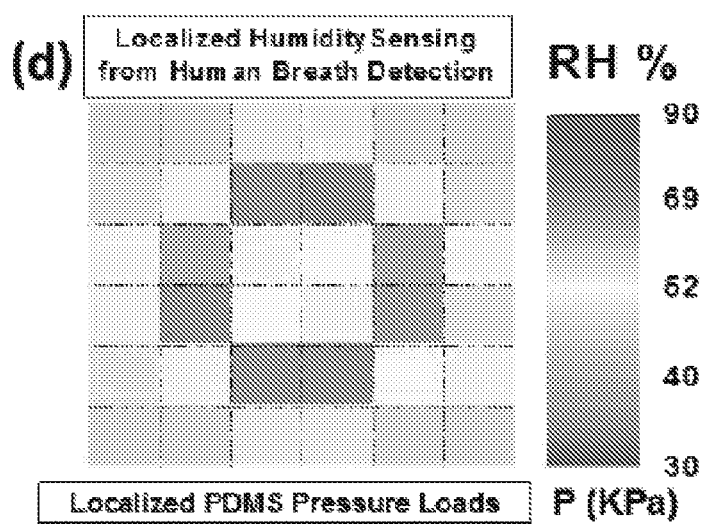

For a second experiment, we simultaneously blew human breath on localized pixels of the paper skin in order to study the capability of identifying separate humidity positions. In order to confine the flow to singular pixels, we used a straw to exert flow on the following pixels: R2-C3, R2-C4, R3-C2, R3-C5, R4-C2, R4-C5, R5-C3, and R5-C4. FIG. 13(d) shows the spatial imaging of the humidity levels detected. We can clearly distinguish high humidity levels ranging from 65% to 75% RH, corresponding to the stimulated pixels. As room conditions correspond to 46% RH, we notice that the surrounding pixels were slightly affected with a detected humidity up to 53% RH, a 7% increase in humidity level. Nevertheless, our sensors showed very good performance with an accurate spatial mapping for temperature and humidity.

Figure 13F:
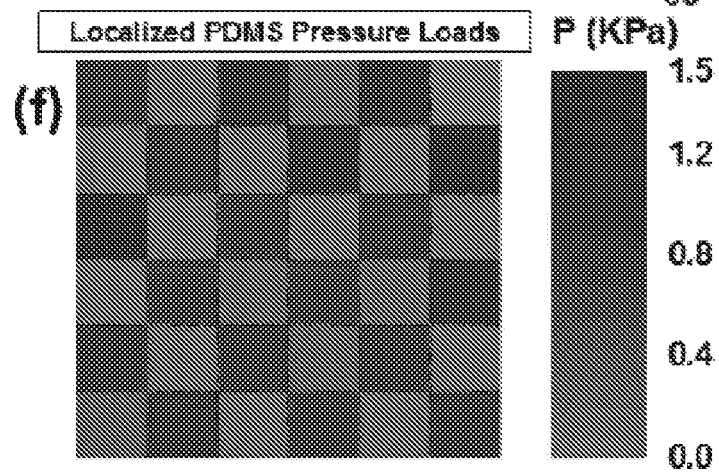
Figure 13G:
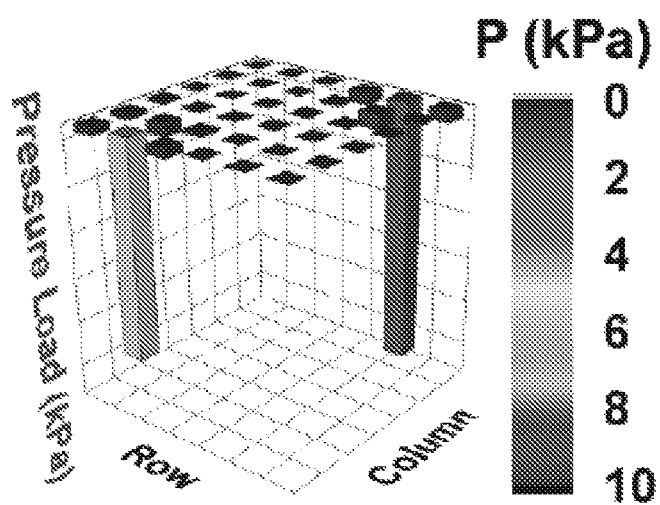

To conduct pressure mapping using the whole array, we applied PDMS weights (0.19 g/piece) on specific pixels, ordered in a pattern similar to that of a "chess board". FIG. 13(f) displays the spatial mapping of pressure detection exerted by the PDMS loads. Sensed pressures ranged from 0.7 kPa to 1 kPa. This variation in measured pressure values is mainly due to the non-uniformity of the pressure sensing film, underlining the non-uniformity of our array. FIG. 13(e) shows the distribution of pixel uniformity in the pressure array. We observe that the capacitance values vary among pixels from 1.5 pF up to nearly 4 pF, where the majority falls under a capacitance of around 3.5 pF, Moreover, since the sensing film consisted of a common dielectric for all pixels, when one pixel is pressed, neighboring pixels slightly varied. To better illustrate this effect, we plot the 3D bars representation corresponding to localized stimuli (8 kPa load) applied on pixels R1-C2 and R6-C5. FIG. 13(g) displays the 3D mapping image, where we can clearly identify detected pressures in the interval of 0.1-0.4 kPa in the neighboring pixels. This is a very negligible variation ranging from 1% to 5% of the total applied pressure load, highlighting the effective location and load detection of our array.

Figure 13H:
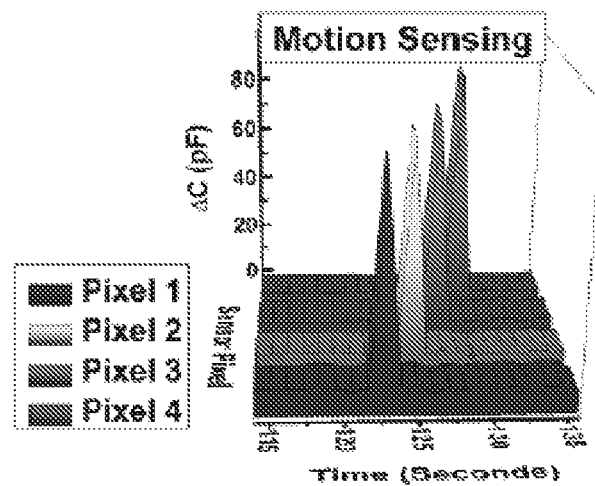

Additionally, we demonstrated the temporal recording of the paper skin and its ability to effectively detect motion direction. This was executed by connecting 4 pixels of the pressure sensor to an "Arduino Lino" microcontroller, interfaced with 'Matlab' software through another code that helped only in reading out the processed information from the serial port. This successfully allowed us to generate and display a real-time histogram plot of the detected movement. FIG. 13(h) illustrates the triggered pixels with time during motion, where we can clearly distinguish separate responses at consecutive times. We successfully demonstrated a pressure-sensing platform efficiently mapping out applied pressure, touch, motion, and proximity, over a large surface area using only paper, cleanroom wipes, and aluminum foil.

Direct comparison between this work and several of the artificial skin platforms being developed by pioneers in the field[15,17,22,23,28,29,37,60-61], shows that our Paper Skin maintains the desirable high performance of sensors, while displaying more valuable features through the integration of various functionalities with the most affordable materials possible. Paper skin shows to be the most inexpensive and advantageous option preserving the required high performance of sensors platform. The demonstrated "paper skin" could simultaneously measure a variety of external stimuli with great precision. The integration of the proposed sensors did not affect the neighboring sensor's ability to independently distinguish external stimuli, which is translated into negligible external effects on sensor sensitivity.

Body-Vitals Monitoring

To demonstrate the "paper skin" potential for wearable health sensing, two pixels of the paper skin array were employed to simultaneously measure heart rate, blood pressure, body temperature and skin hydration. In order to maximize the accuracy of our readings, we have used the in-plane array design, where all the sensors are integrated next to one another. Highly sensitive pressure sensors enable real-time monitoring of arterial blood pulses as well as heart rate measurement from pressure and time-resolved responses.

Figure 14A:
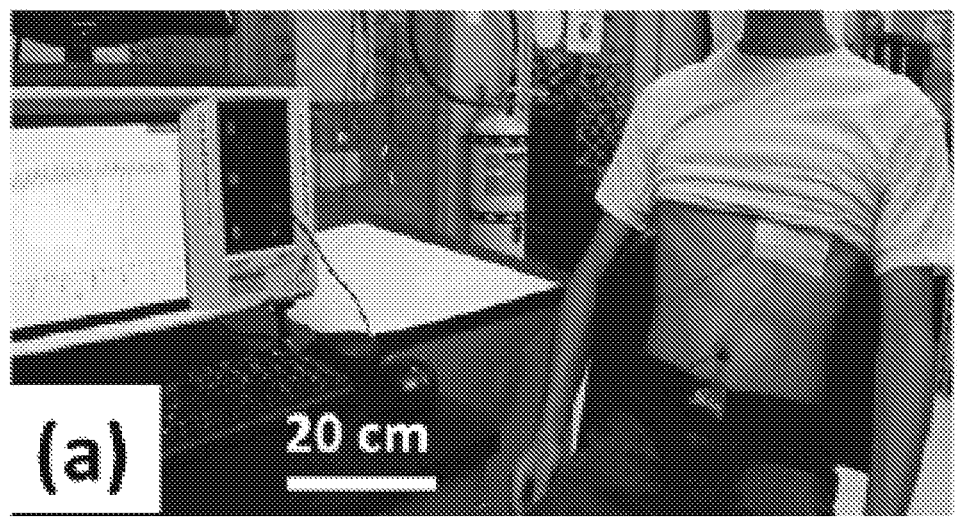
Figure 14B:
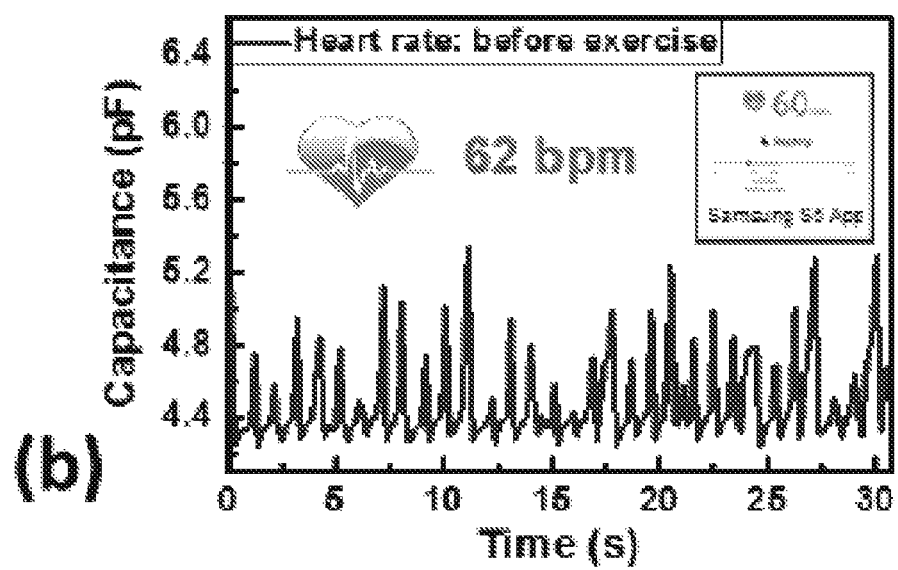
Figure 14C:
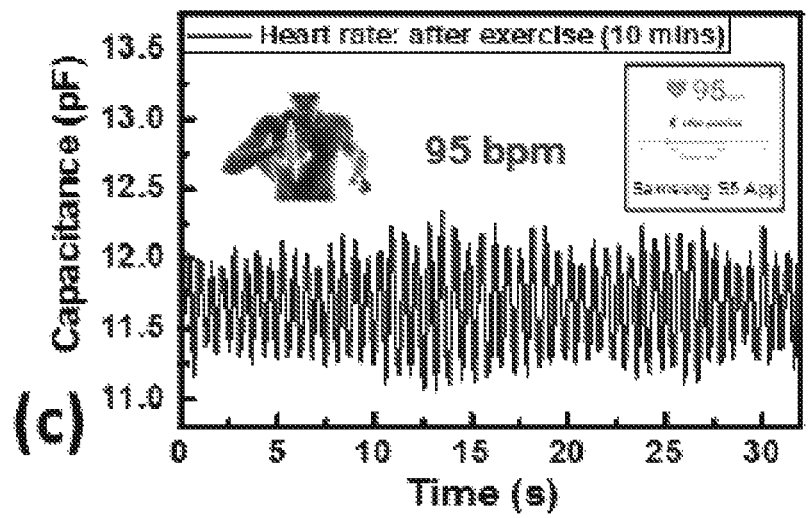

Heart rate detection before and after exercise was detected from the direct heart pulses, positioning the paper skin on the right side of the chest, as seen in FIG. 14(a). Measurements were then compared to the built-in heart monitor of Samsung S5 smartphone, clearly displaying a normal average resting heart rate between 61 and 76 bpm (beats per minute), and an after exercise rate interval between 98 and 166 bpm. Our device accurately collected heart rate measurements with 62 bpm before exercise (FIG. 14(b)) and 95 bpm after 10 minutes of physical exercise (FIG. 14(c)). Heart beat dynamics can reveal many things including real-time personalized emotional responses and stress detection. Stress can be measured through the change in the interval between heartbeats, known as heart rate variability (HRV) characterized by pressure peak-to-peak time. Heart rate variability is one of the most robust, non-invasive measures of stress response and is designated by a reduction in HRV (i.e. monotone beats frequency).

Figure 14D:
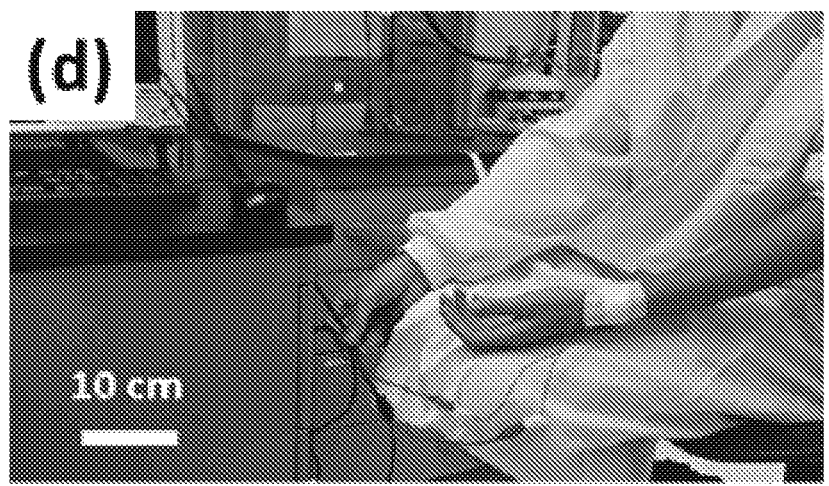
Figure 14E:
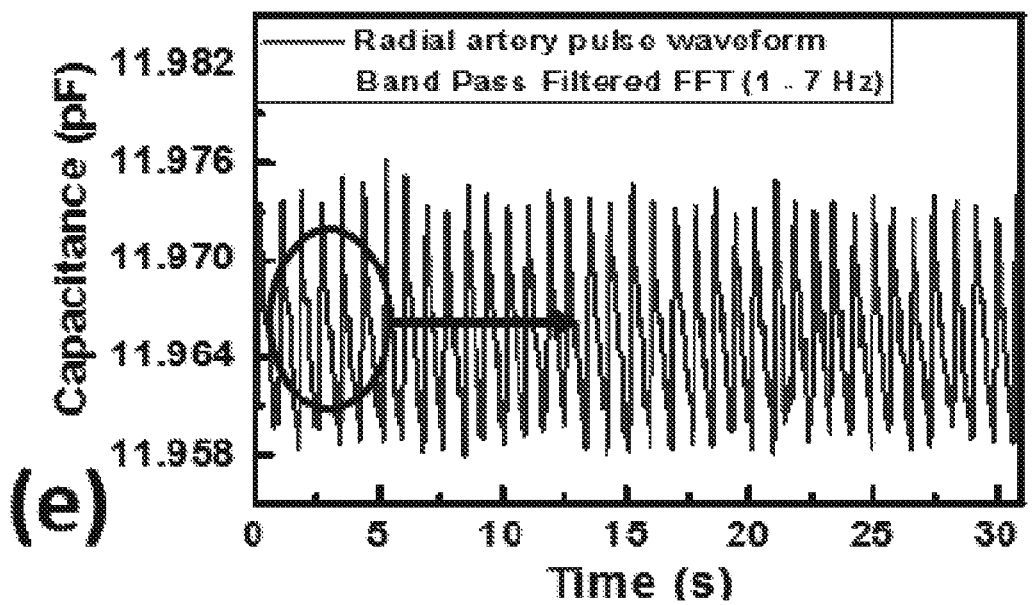
Figure 14F:
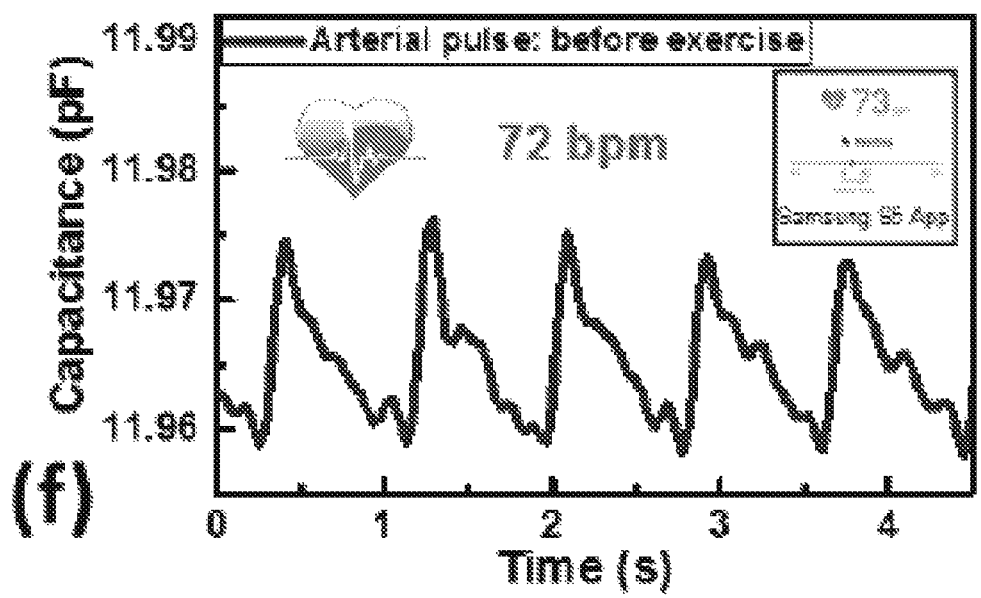

To detect blood pressure, the paper skin was positioned around the left-hand wrist in order to detect radial artery pulses, as shown in FIG. 14(d). Under normal resting conditions, we were able to identify the radial artery pulse waveform over a period of 30 s (FIG. 14(e)), as well as efficiently displaying a heart rate of 72 bpm (FIG. 14(f)), consistent with the expected results. The arterial waveform is characterized by clearly resolvable peaks P1, P2, and P3, respectively corresponding to early systolic blood pressure (SBP), late systolic augmentation shoulder (late SBP), and early diastolic blood pressure (early DBP) which is preceded by a Dicrotic notch (closure of aortic valve) (FIG. 14(g)). The observed three waves within the pulse envelope respectively correspond to an incident wave generated by blood flow (P1) and two reflected waves, one from the hand region (P2) and a later-arriving wave from the lower body (P3)[47]. These variations are caused by constitution of the blood pressure from the left ventricle contracts and reflective waves from the lower body. A key advantage of acquiring the complete arterial pulse waveform is that several hemodynamic parameters can be directly calculated or estimated in real time such as arterial indexes, stroke volume variation, and cardiac output, enabling a profound portrayal of a patient's cardiovascular health and well-being[48]. Arterial stiffness is one of the major health concerns leading to arterial clogging, diabetes, and hypertension. Thus, it is established as a highly reliable predictive parameter for cardiovascular diseases. Arterial stiffness can be identified from the peaks positions in the radial artery waveform. As the elastic arteries become stiffer, pulse wave velocity (PWV) increases and the reflected wave from the lower body returns earlier to the radial artery, migrates up the pressure wave towards peak systolic pressure, and thus causes a decrease in TDVP (digital volume pulse time) and an increase in arterial stiffness index $AI_r$[49]. Arterial stiffness can thus be analyzed from the arterial augmentation stiffness index (AIr), diastolic augmentation index (DAIr), digital volume pulse (DVP), and PWV (Equation 1):

$$AI_r = P2/P1 \quad (1.1)$$

$$DAI_r = P3/P1 \quad (1.2)$$

$$\Delta T_{DVP} = t_{p2} - t_{p1} [s] \quad (1.3)$$

$$PWV = \text{body length}/(t_{SBP} - t_{DBP}) \ [m/s] \quad (1.4)$$

Figure 14G:
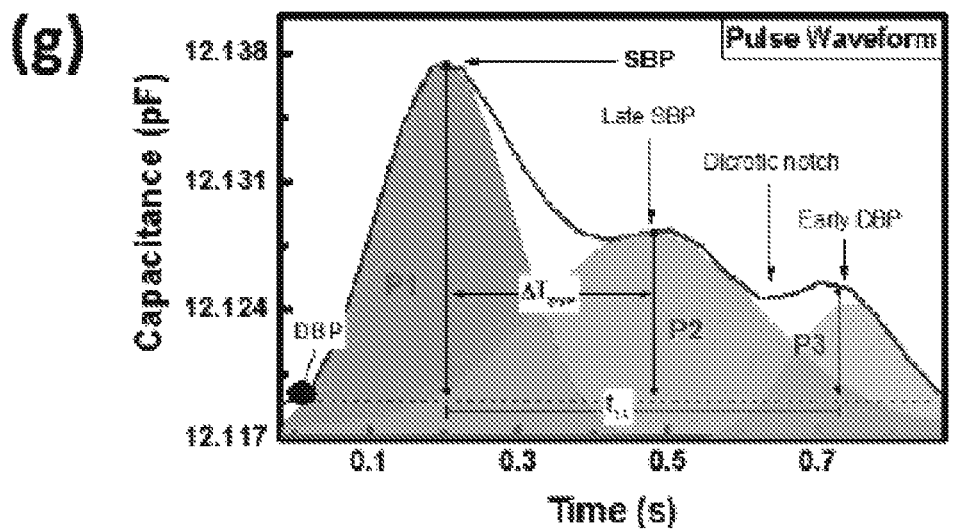

From the measured radial artery waveform, we calculate an average $AI_r$=0.52 (52%), $DAI_r$=0.37(37%), $\Delta T_{DVP}$=270 ms with DVP=5.83 m/s, and PWV=6.07 m/s (FIG. 14(g)). These numbers are highly related to the age of people, and show to be consistent for a healthy young male in his twenties[49]. Note that for PWV and DVP calculations, the path length is approximated to the person's height. The time difference $t_{13}$ between the arrival of the primary systolic pulse (P1) and the reflection pulse (P3) is also a measure of arterial stiffness that tracks changes in arterial pulse pressure and beat-by-beat frequencies, and is measured to be $t_{13}$=520 ms (FIG. 14(g)).

Figure 14H:
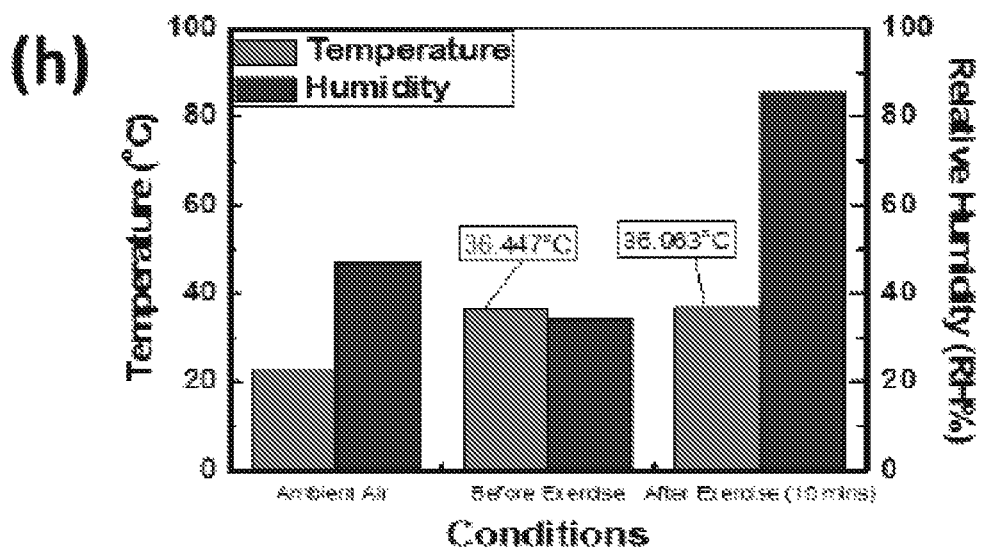

Simultaneously, body temperature and relative humidity of the skin were collected before and after exercise. We observed a resting body temperature of 36.45° C. with a slight rise of nearly 0.5° C. directly after exercise, attributed to the loss of heat from the 70% of energy powering our muscles. The relative humidity of the skin before exercise is measured to be 35% RH at an ambient humidity of 46% and temperature of 23° C. (FIG. 14(h)). This result is in agreement with the expected values described in the literature for normal skin hydration levels[50]. After exercise, our heart pumps the heat in the blood from the muscles to the skin, leading to sweat. This highlights the observed increase in relative skin humidity up to 85% (FIG. 14(h)). Our results demonstrate that the subtle differences in blood pulses, body temperature and skin humidity, could be precisely resolved with the presented "Paper Skin", indicating its potential to serve as a low-cost wearable device for mobile health monitoring and remote diagnostics applications.

Conclusion

Using only off-the-shelf resources, we provide a paper-based skin capable of detecting temperature, humidity, pH, pressure, touch, motion and proximity at a record-breaking distance of 13 cm. The fabricated sensors show reliable and consistent results, and the pressure array displayed exceptional capability in differentiating multiple external stimuli. The simplistic fabrication process and low-cost materials used in this work make this flexible platform the lowest cost and accessible to anyone, without affecting performance, in terms of response and sensitivity. We further show that our "paper skin" can efficiently resolve arterial and heart rate pulse waveforms, providing deep information about a patient's well-being. Additionally, the proximity and motion features obtained in this work illustrate the possibility for paper-based touchless motion systems, bringing the user-to-computer interface experience to a whole new level. Paper Skin is an affordable all-in-one flexible sensing platform, applicable for emerging applications, such as health monitoring, 3D touchscreens, and human-machine interfaces, where sensing diversity, surface adaptability, and large-area mapping are all essential. Future works include analysis of performance characteristics and reliability of the fabricated skin under various mechanical deformation (flexing, stretching, etc.). Although further sophistication is possible, at the present stage the demonstrated "paper skin" integrates the maximum sensory functions of a human skin and shows cost effective health monitoring for wide deployment.

EXAMPLES

Fabrication Process of Sensors

Temperature sensors: We draw 1×1 cm² resistive temperature sensors using silver ink pen (Circuit Scribe) on a Post-it™ Note. The resistor has line width of 1 mm and 1 mm line separation. For the aluminum foil based temperature sensor, we cut a 3×1 cm² aluminum foil sheet in the shape of a resistor, with 2 mm line width and 2 mm line separation.

Humidity sensors: Post-it™ paper acts as the sensing film and the substrate. We draw 1×1 cm² interdigitated electrodes structure using silver ink pen, with 2 mm finger width and 1 mm finger separation. Then we protect the surface with a 1.5×1.5 cm² sheet of Kimtech™ wipe, taping the edges on the paper substrate using 3M™ adhesive tape.

pH sensor: In this case, Post-it™ note acts only as the flexible substrate. Interdigitated electrodes are outlined with the silver conductive pen, with 3 mm finger width and 2 mm finger separation. After it's completely dried, we draw on top a 3×3 cm² sheet of sensing film using a simple graphite pencil of grade HB. We make sure that the layer is uniformly distributed and colored.

Pressure sensors: We have implemented two pressure designs. The first design is a simple parallel plate capacitor structure. First, we use the post-it paper as a substrate for keeping the final structure flat and stable. Then, we deposit the first metal layer, a 1×1 cm² sheet of aluminum foil, taped on the paper using 1×1 cm² sheet of double-sided adhesive tape. Then, we proceed by depositing another layer of double-sided tape (d=90 µm) in order to attach the dielectric material on top. In this case, we use two different types of dielectric materials: a porous sponge ($d_{sponge}$=0.7 cm) and 100% polypropylene microfiber cleanroom wipe ($d_{fiber\text{-}wipe}$=600 µm) (Berkshire™ PRO-WIPE™ 880). Finally, we deposit once again a layer of double-sided adhesive tape to fix the 1×1 cm² aluminum foil top electrode. As for the second pressure sensor design, we introduce a 90 μm air gap into the original capacitive pressure structure described above. The air gap is created through the placement of anchors on either side of the sensor: after depositing the first metal electrode, we place two double-sided tape stripes of 2 mm width on the edges of the capacitor. Then we proceed with the steps as described in the first design, using microfiber cleanroom wipe ($d_{fiber-wipe}$=600 μm) for the dielectric material.

Paper Skin Array: For the 6×6 "paper skin" assembly, we overlay three layers of sensors arrays on top of each other. Each layer is comprised of one sensor type, with 1 cm² pixel size and 1 mm pixel separation. The first bottom array consists of air-gap based pressure sensors, where the bottom electrode acts as a common ground for all pixels, and the shared dielectric consists of a large 11×11 cm² cleanroom wipe sheet. The second layer consists of an array of silver ink based temperature sensors, and finally the third layer is an array of humidity sensors with an optional protective KIMTECH™ wipe on top. The three layers are stacked in such a way that pressure, temperature and humidity pixels are exactly on top of each other. For each layer, we have one sensor per pixel, giving specific information independently from the rest of the array, Every single pixel can be accessed, ultimately allowing for simultaneous localized sensing, Proximity Sensing Methods Maxwell's equations provide a complete description of the interactions among charges, currents, electric fields, and magnetic fields. All the properties of the fields can be obtained by mathematical manipulations of these equations. If the distribution of charges and currents is given, then these equations uniquely determine the corresponding fields. When a magnetic field moves through a conductor (aluminum foil), eddy currents are induced on the surface of the aluminum foil due to the magnetic field's movement. Applying an AC voltage with high frequency to a parallel plate capacitor generates internal electric and magnetic fields in between the two conductive plates. The setup can be regarded as a parallel circuit of a resistor with resistance R and a capacitor with capacitance C. In the most general case, the surface spanned by the integration path of the magnetic field can intercept current and electric flux, and is described by:

$$\int_{path} \vec{B} \cdot \vec{dL} = \mu_0 I + \mu_0 \varepsilon_0 \frac{d\varphi_E}{dt}; \varphi_E = EA = \frac{Q}{\varepsilon_0}$$

Where $\varphi_E$ the electric flux through the surface, B is the magnetic field flux, I is the generated current, Q is the total charge of the capacitor, and A the area of the parallel plates, The electric field between the capacitor plates is equal to $\varphi_{E(t)}$, and the electric flux through the capacitor is therefore equal to:

$$\varphi_E(t) = AE(t) = \frac{AV_0 \sin(\omega t)}{d}$$

The charge on the capacitor can be thus described by:

$$Q(t) = CV(t) = \frac{\varepsilon_0 A V_0}{d} \sin(\omega t)$$

And the total current is therefore equal to:

$$I_{tot}(t) = I_R(t) + I_C(t) = V_0 \left\{ \frac{1}{R} \sin(\omega t) + \frac{\varepsilon_0 A \omega}{d} \cos(\omega t) \right\}$$

The magnetic field lines inside the capacitor will form concentric circles. The path integral of the magntic field around a circle of radius r is equal to:

$$\int_{path} \vec{B} \cdot \vec{dL} = 2\pi r B(r) = \mu_0 V_0 \left( \frac{1}{R} \sin(\omega t) + \frac{\varepsilon_0 \pi r^2 \omega}{d} \cos(\omega t) \right)$$

And the strength of the magnetic field can be finally defined by:

$$B(r) = \frac{\mu_0}{2\pi} V_0 \left( \frac{1}{rR} \sin(\omega t) + \frac{\varepsilon_0 \pi r \omega}{d} \cos(\omega t) \right)$$

Electrical Characterization Setup

Real-time resistive measurements: For resistive time study, sensors were tested using Keithley 4200™ interface capable of real-time measurements and a semi-automated cascade probe station. To characterize temperature sensors, we apply a current bias of 10 mA and we sample voltage readings every 130 ms, for a total sampling number of 400. This sampling rate was limited by our tool given that we were running in "Quiet" mode in order to reduce noise interference. Voltage change is thus monitored with respect to time, while current is maintained constant. Resistance change can be calculated by Ohm's law:

$$R[\text{in } \Omega] = \frac{V[\text{in V}]}{I[\text{in A}]}$$

Simultaneous sensing of pixels for spatial mapping was achieved through the probing of several pixels and collection of measurements simultaneously through the Keithley software.

Real-time capacitive measurements: Capacitive time study was performed for both humidity and pressure sensors. Again, we use Keithley 4200™ interface with CV measurements capability, at an applied 1 MHz modulation frequency and 100 mV AC voltage. In this manner, we can define the capacitive reactance ($X_c$, in Ω) which is inversely proportional to the frequency (w, in radians/sec, or f, in Hz) and capacitance (C, in Farads) by:

$$X_C = \frac{1}{j \cdot \omega \cdot C} = \frac{-j}{\omega, C} \left[ \frac{\text{rad}}{s}, F \cdot \Omega \right]$$

And the total charge Q (in Coulombs) stored on a capacitor's plates described by:

$$Q = C, V[F, V]$$

Where V is the applied voltage across the device.

Humidity sensing: For measuring capacitance associated to different humidity levels, we perform a CV plot by sweeping voltage from 0V to 5V with a step of 0.05 V. Finally, time study is performed by sampling 400 points every 130 ms. Our temporal resolution is limited by our sampling rate in "Quiet mode". As for the water vapor experiment, we boiled tap water in a beaker glass and brought it in proximity to our sensor (FIG. 9(d)). In order to direct the water vapor towards the sensor, we use a wind tunnel setup in which the fan is installed in a way to suck the air from the sensor side towards the wind tunnel in a laminar manner, allowing the vapor to flow across the surface of our sensor (FIG. 3i). For spatial mapping of humidity in response to human breath, external stimulus was exerted simultaneously on different pixels through a drinking straw, and data was collected through the Keithley setup. This allows to properly confine the humid breath into one pixel.

Pressure/Force sensing: We prepare polydimethylsiloxane (PDMS) (Sylgard 184™, Dow Corning) weights with mass 0.19 g/piece, to use them as pressure loads for testing the sensitivity of our devices. Correspondingly, capacitance—voltage measurements are performed with a sweeping voltage from −5 V to 5 V at 1 MHz frequency. And real-time sensing is performed in the same manner as for the humidity sensor.

Flow pressure detection was performed by flowing compressed air through a 1 mm in diameter nozzle. Normal flow velocities were measured using a digital anemometer of 0.1 m/s accuracy. The specified velocity magnitudes are that of a normal velocity vector, normal to the sensor's plane (90° orientation), For different flow orientations, we use a protractor in order to evaluate the angle of the flow with respect to the plane of our pressure sensor.

Finally, proximity sensing was evaluated using the same exact real-time sensing parameters as previously. For distance referencing, we vertically install a ruler in proximity of the probe station chuck. We make sure that the zero value of the ruler corresponds to the surface level of our pressure sensor. Then we carefully collect real-time measurements while slowly approaching the tip of an index finger along the length of the ruler.

Body vitals monitoring: Measurements were executed as described in the above section, However in this case, we have changed the sampling rate down to 30 ms time step. This was necessary mostly to capture heart beats after exercise. This was only possible by operating in "fast mode" which has introduced a lot of noise. Therefore, for the after exercise heart rate plot, we ran a Fast Fourier Transform (FFT) to identify the available and necessary range of frequencies. Based on our results, we post-processed the original plot using band bass filtering for frequencies in the interval of [1-7 Hz].

Capacitance Sensing Code Principle for 'Arduino Uno' Microcontroller

Charging the capacitor stores energy in the electric field between the capacitor plates. The rate of charging is typically described in terms of a time constant RC as follows:

$$Q = CV_b[1 - e^{-t/RC}]; V_b = I \cdot R + \frac{Q}{C}$$

Thus, change in capacitance (C) can be measured by measuring the change in time constant of RC with known value of resistance (R). As R generates lots of noise in circuits, it's not a preferred method to measure small changes in C especially in the range of pF. Therefore, we have used switched capacitance technique to reliably measure small changes in capacitance using Arduino UNO. This technique is similar to standard RC time constant technique in the way that R is virtually replaced by the combination of a switch and unknown C sensed by the sensor ($C_{sen}$). A constant value of integrating C ($C_{int}$) is used to store the charge in multiple switching cycles. One complete switching cycle consists of charging the $C_{sen}$ keeping the $C_{int}$ in high impedance state followed by transferring the charge from $C_{sen}$ to $C_{int}$. This switching sequence effectively transfers charge from applied voltage $V_s$ to $C_{int}$. The number of switching cycles required to charge $C_{int}$ to a certain voltage depends upon the value of $C_{sen}$ (or equivalent $R_{sen}$) and were measured using Arduino UNO in our case. Higher number of switching cycles corresponds to smaller value of $C_{sen}$ and vice versa. Also $R_{cal}$ was used to calibrate the circuit while P2 represents an analog pin which compares $C_{int}$ voltage with a pre-defined reference ($V_{ref}$). P1, P3 and P4 are digital pins being controlled by the controller program to alter between the charging and transfer modes of a switching cycle. This circuit was replicated 4 times to simultaneously demonstrate motion detection from the change in capacitance of multiple pixels on the smart skin.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

REFERENCES

1 Han, J.-W., Kim, B., Li, J. & Meyyappan, M. A carbon nanotube based ammonia sensor on cellulose paper. *RSC Adv.* 4, 549-553 (2014).
2 Koga, H. et al. Uniformly connected conductive networks on cellulose nanofiber paper for transparent paper electronics. *NPG Asia Mater,* 6, e93 (2014).
3 Lessing, J. et al. Inkjet Printing of Conductive Inks with High Lateral Resolution on Omniphobic "RF Paper" for Paper-Based Electronics and MEMS. *Adv. Mater.* 26, 4677-4682 (2014).
4 Russo, A. et al. Pen-on-Paper Flexible Electronics, *Adv. Mater,* 23, 3426-3430 (2011).
5 Siegel, A. C., Phillips, S. T., Wiley, B. J. & Whitesides, G. M. Thin, lightweight, foldable thermochromic displays on paper. *Lab Chip* 9, 2775-2781 (2009).
6 Tobjörk, D. & Österbacka, R. Paper electronics. *Adv. Mater.* 23, 1935-1961 (2011).
7 Tan, E. L., Ng, W N., Shao, R., Pereles, B. D. & Ong, K. G. A wireless, passive sensor for quantifying packaged food quality. *Sensors* 7, 1747-1756 (2007).

8 Unander, T. & Nilsson, H.-E. Characterization of printed moisture sensors in packaging surveillance applications. *IEEE Sens. J.* 9, 922-928 (2009).

9 Wang, L. et al. Simple, Rapid, Sensitive, and Versatile SWNT—Paper Sensor for Environmental Toxin Detection Competitive with ELISA. *Nano Lett.* 9, 4147-4152 (2009).

10 Yun, S. & Kim, J. Multi-walled carbon nanotubes-cellulose paper for a chemical vapor sensor. *Sens. Actuators, B.* 150, 308-313 (2010).

11 Manzoli, A. et al. Low-cost gas sensors produced by the graphite line-patterning technique applied to monitoring banana ripeness. *Sensors* 11, 6425-6434 (2011).

12 Jang, J., Ha, J. & Cho, J. Fabrication of Water-Dispersible Polyaniline-Poly (4-styrenesulfonate) Nanoparticles For Inkjet-Printed Chemical-Sensor Applications. *Adv. Mater.* 19, 1772-1775 (2007), 13 Lakafosis, V. et al. Progress towards the first wireless sensor networks consisting of inkjet-printed, paper-based RFID-enabled sensor tags, *Proc. IEEE.* 98, 1601-1609 (2010).

14 Hammock, M. L., Chortos, A., Tee, B. C. K., Tok, J. B. H. & Bao, Z. 25th Anniversary Article: The Evolution of Electronic Skin (E-Skin): A Brief History, Design Considerations, and Recent Progress, *Adv. Mater.* 25, 5997-6038 (2013).

15 Harada, S. et al. Fully Printed Flexible Fingerprint-like Three-Axis Tactile and Slip Force and Temperature Sensors for Artificial Skin. *ACS Nano* (2014).

16 Park, S. et al. Stretchable Energy-Harvesting Tactile Electronic Skin Capable of Differentiating Multiple Mechanical Stimuli Modes, *Adv. Mater.* 26, 7324-7332 (2014).

17 Schwartz, G. et at Flexible polymer transistors with high pressure sensitivity for application in electronic skin and health monitoring. *Nat. Commun.* 4, 1859 (2013).

18 Sun, J. Y., Keplinger, C., Whitesides, G, M. & Suo, Z. Ionic skin. *Adv. Mater.* 26, 7608-7614 (2014).

19 Wang, X., Gu, Y., Xiong, Z., Cui, Z. & Zhang, T. Silk-Molded Flexible, Ultrasensitive, and Highly Stable Electronic Skin for Monitoring Human Physiological Signals. *Adv. Mater.* 26, 1336-1342 (2014), 20 Gao, L, et al. Epidermal photonic devices for quantitative imaging of temperature and thermal transport characteristics of the skin. *Nat. Commun.* 5 (2014).

2 Huang, X. et al. Materials and Designs for Wireless Epidermal Sensors of Hydration and Strain, *Adv. Fund. Mater.* 24, 3846-3854 (2014).

22 Kim, J. et al. Stretchable silicon nanoribbon electronics for skin prosthesis. *Nat. Common.* 5 (2014).

23 Ramuz, M., Tee, B. C. K., Tok, J. B. H. & Bao, Z. Transparent, Optical, Pressure-Sensitive Artificial Skin for Large-Area Stretchable Electronics, *Adv. Mater.* 24, 3223-3227 (2012).

24 Segev-Bar, M., Landman, A., Nir-Shapira, M., Shuster, G, & Haick, H. Tunable touch sensor and combined sensing platform: toward nanoparticle-based electronic skin. *ACS Appl. Mater, Interfaces* 5, 5531-5541 (2013).

25 Sekitani, T. & Someya, T. Stretchable, Large-area Organic Electronics. *Adv. Mater.* 22, 2228-2246 (2010).

26 Someya, T. Building bionic skin. *IEEE Spectrum* 50, 50-56 (2013).

27 Someya, T. et al. Conformable, flexible, large-area networks of pressure and thermal sensors with organic transistor active matrixes, *Proc. Natl. Acad. Sci. U.S.A.* 102, 12321-12325 (2005).

28 Takahashi, T., Takei, K., Gillies, A. G., Fearing, R. S. & Javey, A. Carbon nanotube active-matrix backplanes for conformal electronics and sensors. *Nano Lett.* 11, 5408-5413 (2011).

29 Takei, K. et al, Nanowire active-matrix circuitry for low-voltage macroscale artificial skin. *Nat. Mater.* 9, 821-826 (2010).

30 Tien, N. T. et al. A flexible bimodal sensor array for simultaneous sensing of pressure and temperature. *Adv. Mater.* 26, 796-804 (2014).

31 Wang, C. et al. User-interactive electronic skin for instantaneous pressure visualization. *Nat. Mater.* 12, 899-904 (2013).

32 Circuit Scribe, http://www.circuitscribe.com/. (2015).

33 Wirtz, P, et al. LMR spectroscopy: a new sensitive method for on-line recording of nitric oxide in breath. *J. Appl. Physiol.* 86, 1075-1080 (1999).

34 Abdullah, S. M., Ahrnad, Z, & Sulaiman, K. A solution-based temperature sensor using the organic compound CuTsPc. *Sensors* 14, 9878-9888 (2014).

35 Gu, L., Huang, Q.-A. & Qin, M. A novel capacitive-type humidity sensor using CMOS fabrication technology. *Sens. Actuators, B* 99, 491-498 (2004).

36 Lee, C.-Y., Hsieh, W.-J, & Wu, G.-W. Embedded flexible micro-sensors in MEA for measuring temperature and humidity in a micro-fuel cell. *J. Power Sources* 181, 237-243 (2008).

37 Chung, V. P., Cheng, C.-L., Yip, M.-C. & Fang, W. A CMOS capacitive vertical-parallel-plate-array humidity sensor with RF-aerogel fill-in for sensitivity and response time improvement. *IEEE Int. Conf. Micro Electro Mech. Syst.* 28th 767-770 (2015).

38 Lin, C.-H., Fu, L.-M. & Lee, C.-Y. MEMS-based humidity sensor based on thiol-coated gold nanoparticles, *IEEE Int. Conf. Nano/Micro Eng. Mot. Syst.,* 9th 191-194 (2014).

39 Yang, T. et al. Fabrication of silver interdigitated electrodes on polyimide films via surface modification and ion-exchange technique and its flexible humidity sensor application. *Sens. Actuators, B* 208, 327-333 (2015).

40 Hizawa, T., Sawada, K., Takao, H. & Ishida, M. Fabrication of a two-dimensional pH image sensor using a charge transfer technique. Sens, *Actuators, B* 117, 509-515 (2006).

41 Lei, N., Li, P., Xue, W. & Xu, J. Simple graphene chemiresistors as pH sensors: fabrication and characterization. *Meas. Sci. Technol.* 22, 107002 (2011).

42 Sheppard, N. F., Lesho, M. J., McNally, P. & Francomacaro, A. S. Microfabricated conductimetric pH sensor. *Sens. Actuators, B* 28, 95-102 (1995), 43 Liu, X. et al. A highly sensitive pressure sensor using a Au-patterned polydimethylsiloxane membrane for biosensing applications. *J. Micromech, Microeng.* 23, 025022 (2013).

44 Cotton, D. P., Graz, I. M. & Lacour, S. P. A multifunctional capacitive sensor for stretchable electronic skins. *IEEE Sens. J.* 9, 2008-2009 (2009).

45 Lipomi, D. J. et al. Skin-like pressure and strain sensors based on transparent elastic films of carbon nanotubes. *Nat. Nanotechnol.* 6, 788-792 (2011).

46 Malik, M. Heart Rate Variability. Ann. Noninvasive Electrocardiol. 1, 151-181(1996).

47 Marwick, T. H. et al, Recommendations on the use of echocardiography in adult hypertension: a report from the European Association of Cardiovascular Imaging 48 Muxfeldt, E. S., Fiszman, R., Castelpoggi, C. H. & Salles, G. F. Ambulatory arterial stiffness index or pulse pressure: which correlates better with arterial stiffness in resistant hypertension? Hypertens. Res. 31, 607 (2008).

49 Fantin, F., Mattocks, A., Bulpitt, C. J., Banya, W. & Rajkumar, C. Is augmentation index a good measure of vascular stiffness in the elderly? *Age Ageing* 36, 43-48 (2007).

50 Mole, R. The relative humidity of the skin. *J. Physiol.* 107, 399-411 (1948), 51 Nave, C. R. Resistor Temperature Dependence, Hyper-Physics, http://hyperphysics.phyastr.gsu.edu.hbase/electric/restmp.html (2001).

52 Yamazoe, N. & Shimizu, Y. Humidity sensors: principles and applications. *Sensors and Actuators* 10, 379-398 (1986).

53 Kimberley-Clark Professional, KIMTECH SCIENCE KIMWIPES, http://www.kcprofessional.com/products/wipers/specialty/kimtech-science/34120-kimtech-science-kimwipes-delicate-task-wipers (2013).

54 Queensland Curriculum & Assessment Authority QCAA, Extended experimental investigation: Electrical conductivity of graphite. https://www.qcaa.qid.edu.au/downloads/senior/snr physics 07 sai electric con duct graphite.pdf (2013).

55 Zang, Y. et al. Flexible suspended gate organic thin-film transistors for ultra-sensitive pressure detection. *Nat. Commun.* 6 (2015).

56 Jung, S, et al. Reverse-Micelle-Induced Porous Pressure-Sensitive Rubber for Wearable Human-Machine Interfaces. *Adv. Mater.* 26, 4825-4830 (2014).

57 Balasubramanian, N. Polyester vs. Polypropylene. http//www.fibre2fashon.com/industryarticle/textile-industry-articles/polyester-vs-polypropylene/polyester-vspolypropylene1.asp (2015).

58 Tomizuka, C. & Sonder, E. Self-diffusion in silver. *Phys. Rev.* 103, 1182 (1956).

59 Agilent Technologies. Material Expansion Coefficients. *Laser and Optics User's Manual* 17, 2-12 (2002).

60 Arumugam, V. et al. Effect of strain rate on the fracture behaviour of skin. *J. BioSci.* 19, 307-313 (1994).20

61 Han, J.-W., Kim, B., Li, J. & Meyyappan, M. Carbon nanotube based humidify sensor on cellulose paper. J. Phys. Chem. C 116, 22094-22097 (2012).

Therefore, the following is claimed:

1. A method of producing a paper based sensor, comprising the steps of:
   providing a conventional paper product to serve as a substrate for the sensor or as an active material for the sensor or both, the conventional paper product not further treated or functionalized;
   applying a conductive ink directly to a first region of the conventional paper product to form a temperature sensor;
   forming two conductive fingers directly on a second region of the conventional paper product and applying a cleanroom wipe over the two conductive fingers to form a humidity sensor; and
   attaching with a tape, to a third region of the conventional paper product, a sponge sandwiched between aluminum foils to form a force sensor.

2. The method of claim 1, wherein the conventional paper product is selected from the group consisting of cellulose fiber based porous structures.

3. The method of claim 1, wherein the temperature sensor has a response of 421 ms and a recovery time of 5.27 s for an exhaled breath of a human.

4. The method of claim 1, wherein the humidity sensor has a response of 1 s and a recovery time of 1.33 s for an exhaled breath of a human.

5. The method of claim 1, further comprising: drawing with a pencil of grade HB an electrode directly on a fourth region of the conventional paper product to form a pH sensor, wherein a resistance of the pH sensor increases with a decrease of a pH of a solution and decreases with an increase of the pH of the solution.

6. The method of claim 1, wherein the force sensor forms an air gap with the conventional paper product.

7. The method of claim 1, wherein the force sensor reaches a saturation at 90 kPa.

8. The method of claim 5, wherein the temperature sensor, humidity sensor, pH sensor and force sensor are next to each other on the conventional paper product.

9. A method of sensing, comprising the steps of:
   providing a conventional paper product to serve as a substrate for the sensing or as an active material for the sensing, the conventional paper product not further treated or functionalized;
   applying a conductive ink directly to a first region of the conventional paper product to form a temperature sensor;
   forming two conductive fingers directly on a second region of the conventional paper product and applying a cleanroom wipe over the two conductive fingers to form a humidity sensor;
   attaching with a tape, to a third region of the conventional paper product, a sponge sandwiched between aluminum foils to form a force sensor;
   placing the conventional paper product with the temperature sensor, the humidity sensor, and the force sensor on a skin of a person; and
   measuring, using the temperature sensor, the humidity sensor, and the force sensor, a change in resistance, a change in voltage, a change in current, a change in capacitance, or a combination of any two or more thereof associated with the skin of the person.

10. The method of claim 9, wherein the conventional paper product is selected from the group consisting of cellulose fiber based porous structures.

11. The method of claim 9, wherein the temperature sensor has a response of 421 ms and a recovery time of 5.27 s for an exhaled breath of a human.

12. The method of claim 9, wherein the humidity sensor has a response of 1 s and a recovery time of 1.33 s for an exhaled breath of a human.

13. The method of claim 9, further comprising: drawing with a pencil of grade HB an electrode directly on a fourth region of the conventional paper product to form a pH sensor, wherein a resistance of the pH sensor increases with a decrease of a pH of a solution and decreases with an increase of the pH of the solution.

14. The method of claim 9, wherein the force sensor further includes an air gap.

15. The method of claim 9, wherein the force sensor reaches a saturation of 90 kPa.

16. The method of claim 13, wherein the temperature sensor, the humidity sensor, the pH sensor and the force sensor are next to each other on the conventional paper product.

17. The method of claim 13, wherein the first to fourth regions are located next to each other on the conventional paper product.

18. The method of claim 9, wherein the humidity sensor and the force sensor are formed entirely with home materials.

19. A paper based sensor comprising:
- a conventional paper product to serve as a substrate for the sensor or as an active material for the sensor or both, the conventional paper product not further treated or functionalized;
- a temperature sensor that includes only a conductive ink formed directly on a first region of the conventional paper product;
- a humidity sensor that includes two conductive fingers directly formed on a second region of the conventional paper product and a cleanroom wipe provided over the two conductive fingers; and
- a force sensor attached with a tape to a third region of the conventional paper product and including a sponge sandwiched between aluminum foils.

20. The paper based sensor of claim 19, wherein the force sensor forms an air gap with the conventional paper product.

\* \* \* \* \*